(12) United States Patent
McKnight et al.

(10) Patent No.: US 10,464,858 B2
(45) Date of Patent: Nov. 5, 2019

(54) NON-AQUEOUS ORGANO LIQUID DELIVERY SYSTEMS CONTAINING DISPERSED POLY (ORGANIC ACIDS) THAT IMPROVE AVAILABILITY OF MACRO AND MICRO-NUTRIENTS TO PLANTS

(71) Applicant: WORLD SOURCE ENTERPRISES, LLC, Charleston (KN)

(72) Inventors: Gary David McKnight, High Point, NC (US); Randall Linwood Rayborn, Burlington, NC (US); Wei Xu, Sugarland, TX (US); Raymond Patrick Perkins, Tierra Verde, FL (US)

( * ) Notice: Subject to any disclaimer, the term of this patent is extended or adjusted under 35 U.S.C. 154(b) by 64 days.

(21) Appl. No.: 15/079,844

(22) Filed: Mar. 24, 2016

(65) Prior Publication Data

US 2016/0332929 A1 Nov. 17, 2016

Related U.S. Application Data

(63) Continuation-in-part of application No. 14/740,327, filed on Jun. 16, 2015.

(60) Provisional application No. 62/160,918, filed on May 13, 2015.

(51) Int. Cl.
| | |
|---|---|
| *A01C 1/06* | (2006.01) |
| *C09D 7/20* | (2018.01) |
| *C05G 3/00* | (2006.01) |
| *C05G 3/08* | (2006.01) |
| *A01N 25/26* | (2006.01) |
| *A01N 25/00* | (2006.01) |
| *C05F 3/00* | (2006.01) |
| *C05G 3/06* | (2006.01) |

(52) U.S. Cl.
CPC ........... *C05G 3/0029* (2013.01); *A01N 25/00* (2013.01); *A01N 25/26* (2013.01); *C05F 3/00* (2013.01); *C05G 3/00* (2013.01); *C05G 3/0023* (2013.01); *C05G 3/0041* (2013.01); *C05G 3/06* (2013.01); *C05G 3/08* (2013.01); *A01C 1/06* (2013.01); *C09D 7/20* (2018.01); *Y02A 40/205* (2018.01); *Y02E 50/343* (2013.01); *Y02P 20/145* (2015.11); *Y02P 60/218* (2015.11); *Y02W 30/47* (2015.05)

(58) Field of Classification Search
CPC .. C05G 3/00; C05G 3/08; C05C 9/005; A01C 21/00; A01G 1/001
See application file for complete search history.

(56) References Cited

U.S. PATENT DOCUMENTS

| | | | |
|---|---|---|---|
| 4,172,072 A | 10/1979 | Ashmead | |
| 4,799,953 A | 1/1989 | Danzig | |
| 4,813,997 A | 3/1989 | Kinnersley | |
| 4,839,461 A | 6/1989 | Boehmke | |
| 4,863,506 A | 9/1989 | Young | |
| 5,047,078 A | 9/1991 | Gill | |
| 5,059,241 A | 10/1991 | Young | |
| 5,350,735 A | 9/1994 | Kinnersley | |
| 5,593,947 A | 1/1997 | Kinnersley | |
| 5,783,523 A | 7/1998 | Koskan | |
| 5,814,582 A | 9/1998 | Koskan | |
| 5,994,265 A | 11/1999 | Barclay | |
| 6,557,298 B2 | 5/2003 | Obert | |
| 6,753,395 B2 | 6/2004 | Sanders | |
| 6,756,461 B2 | 6/2004 | Sanders | |
| 6,818,039 B2 | 11/2004 | Sanders | |
| 7,001,869 B2 | 2/2006 | Johnson | |
| 8,016,907 B2 | 9/2011 | Sanders | |
| 8,025,709 B2 | 9/2011 | Sanders | |
| 8,043,995 B2 | 10/2011 | Sanders | |
| 8,519,009 B2 * | 8/2013 | Rodriguez-Kabana | A01N 35/02 504/348 |
| 8,888,886 B1 * | 11/2014 | Whitehurst | C05G 3/08 252/182.12 |
| 9,096,476 B2 * | 8/2015 | Roberts | C05G 3/00 |
| 9,096,516 B2 * | 8/2015 | Sugiura | C07D 207/267 |
| 2009/0270548 A1 * | 10/2009 | Steinmetz | C08G 18/0823 524/504 |

(Continued)

FOREIGN PATENT DOCUMENTS

| | | | |
|---|---|---|---|
| CN | 101391919 | * | 3/2009 |
| CN | 102079670 | * | 6/2011 |

*Primary Examiner* — Wayne A Langel
(74) *Attorney, Agent, or Firm* — Ben Schroeder Law, PLLC

(57) ABSTRACT

The present invention relates to improving the efficiency of man-made and/or natural organic-based animal manure fertilizers by administration of formulations containing poly (organic acids), [P(OA)]s, and/or their salts dispersed in a Non-aqueous Organic Solvent Delivery System (NOSDS). Utilizing a NOSDS allows for coating all components in a fertilizer formulation including but not limited to Urea, Manure, mono-ammonium phosphate (MAP), di-ammonium phosphate (DAP), solid micronutrients such as lime, zinc chloride, etc.) with a layer of [P(OA)]s and/or their salts that liberates, in a plant available form, the micronutrient metals and macronutrients, that are bound as insoluble salts and complexes in the soil. The carboxylic groups of a [P(OA)] that can exist within the [P(OA)] as carboxylic acids, carboxylic anhydrides and/or carboxylic imides, dispersed within the NOSDS, can be neutralized with one or more metals in the form of elemental metals, metal oxides, metal hydroxides, metal alkylates and metal carbonates and/or nitrogen containing compounds such as ammonia, ammonium hydroxide or organoamines to form a stable dispersion that can contain completely complexed micronutrients and provide the vehicle for the delivery of these nutrients to soils and/or as a coating to the surfaces fertilizer granules and seeds.

21 Claims, No Drawings

(56) References Cited

U.S. PATENT DOCUMENTS

| | | | |
|---|---|---|---|
| 2012/0312059 A1* | 12/2012 | Killick | C05D 9/02 |
| | | | 71/23 |
| 2014/0037570 A1* | 2/2014 | Whitehurst | C05C 9/005 |
| | | | 424/76.6 |
| 2014/0090432 A1* | 4/2014 | McKnight | C05G 3/0041 |
| | | | 71/28 |
| 2014/0179520 A1* | 6/2014 | Haschemeyer | C05B 17/00 |
| | | | 504/101 |
| 2015/0101379 A1* | 4/2015 | Gabrielson | C05C 9/00 |
| | | | 71/28 |
| 2015/0299061 A1* | 10/2015 | Catto | C05C 9/005 |
| | | | 504/241 |

* cited by examiner

NON-AQUEOUS ORGANO LIQUID DELIVERY SYSTEMS CONTAINING DISPERSED POLY (ORGANIC ACIDS) THAT IMPROVE AVAILABILITY OF MACRO AND MICRO-NUTRIENTS TO PLANTS

The present invention claims priority under 35 USC 119(e) and 35 USC 120 to U.S. Provisional No. 62/160,918 filed May 13, 2015 and to U.S. application Ser. No. 14/740,327 filed Jun. 16, 2015, the entire contents of which are incorporated by reference in their entireties.

FIELD OF INVENTION

The present invention relates to improving the efficiency of man-made and/or natural organic-based animal manure fertilizers by administration of formulations containing poly (organic acids), [P(OA)]s, and/or their salts dispersed in a Non-aqueous Organic Solvent Delivery System (NOSDS). Utilizing a NOSDS allows for coating all components in a fertilizer formulation including but not limited to Urea, Manure, mono-ammonium phosphate (MAP), di-ammonium phosphate (DAP), solid micronutrients such as lime, zinc chloride, etc.) with a layer of [P(OA)]s and/or their salts that liberates, in a plant available form, the micronutrient metals and macronutrients, that are bound as insoluble salts and complexes in the soil. The carboxylic groups of a [P(OA)] that can exist within the [P(OA)] as carboxylic acids, carboxylic anhydrides and/or carboxylic imides, dispersed within the NOSDS, can be neutralized with one or more metals in the form of elemental metals, metal oxides, metal hydroxides, metal alkylates and metal carbonates and/or nitrogen containing compounds such as ammonia, ammonium hydroxide or organoamines to form a stable dispersion that can contain completely complexed micronutrients and provide the vehicle for the delivery of these nutrients to soils and/or as a coating to the surfaces fertilizer granules and seeds. The metal or metal portions of one of the reactants can further be defined for this invention as Na, K, Mg, Ca, Fe, Zn, Mn, Cu, Co, Mo, or Ni. Organoamine is one or more of the group consisting of mono $C_{1-6}$ amine, di $C_{1-6}$ amine, tri $C_{1-6}$ amine, mono ethanol amine, diethanol amine, triethanol amine, monoisopropyl amine, diisopropyl amine, triisopropyl amine, diethyl amine, diethylene triamine, triethyl tetraamine, tetraethyl pentamine. It has also been discovered that [P(OA)]s and/or their salts can be produced in situ in a NOSDS utilizing organic acids and/or esters monomers dispersed/suspended within the NOSDS, heated to a polymerization temperature with or without catalyst and then neutralized/reacted with one or more macronutrients and/or micronutrients. The liquid compositions of [P(OA)]s in a NOSDS and the methods to produce a [P(OA)] within a NOSDS results in a flowable, low moisture liquid that can be readily mixed with liquid fertilizers or applied safely, quickly, evenly and economically on the surface of solid fertilizer granules, soil and seeds.

BACKGROUND OF THE INVENTION

Macronutrients (N, K, Ca, Mg, P, and S) and Micronutrients (Fe, B, Mn, Zn, Cu, Mo, Co, and Ni) are crucial to a plant's growth, development, disease resistance and various metabolic pathways such as photosynthesis. Plant available micronutrient insufficiencies are due to traditional farming methods that have exhausted the soil and to the micronutrient metals existing as water insoluble salts and complexes. Many of the water insoluble forms in the soil involve a metal cation and boron, sulfur, or phosphorous based anions. A deficiency in micronutrients results in poor plant growth and development and thus in diminished yields (Mortvedt 1990). Plant requirements for many of the micronutrients can be as low as parts/million in the plant tissue. It is known that increasing the plant available micronutrient metal ions by addition of complexed metal ions to the soil or to plant foliage or by freeing up micronutrients, bound in the soil as an insoluble salts or complexes, in a plant absorbable form can help to significantly alleviate soil deficiencies and assist in development, growth, and disease resistance of the plants.

Phosphorous is second to nitrogen as the most limiting macronutrient. In the case of phosphorus fertilizer, 40% of landscape soil is considered to contain inadequate levels of phosphorus for woody plant growth. Moreover, most of the phosphorus in the soil is largely inaccessible as it exists in a form that is not soluble in water and thus is not readily available to plants. In some cases, only 0.01% of the total soil phosphorus is in the form of a water soluble ion, the only form which can be absorbed by the plant. Adequate and accessible soil phosphorus is essential for optimal crop yields. Phosphorus enables a plant to store and transfer energy, promotes root, flower and fruit development, and allows early maturity. Phosphorus is also involved in many processes critical to plant development such as photosynthesis where plants utilize organic phosphorous compounds when converting sunlight to energy. Without enough phosphorus present in the soil, plants cannot grow sufficient root structure, which is key to the plant's ability to absorb water and nutrients from the soil. Moreover, woody plants, without sufficient root structure cannot maintain an equilibrium between roots and shoots, which is key to surviving drought, windy weather, and/or pests. Many of the nutrients required by plants are locked into salts and complexes that are water insoluble and therefore not plant available. To overcome these challenges, the agriculture industry has turned to chelates and anionic based polymers to form water soluble complexes with metal cations such as the micronutrients Ca, Mg, Mn, Fe, Cu, Co Ni, Zn, and Mo resulting in freeing up bound macronutrients such as phosphorous. The current delivery system technology of the chelates and polymer based products is water. Water is not only an excellent solubilizing/dispersing medium for chelates and [P(OA)]s, but can solvate a high load of water soluble metal salts. However, the use of water soluble metal salts can form insoluble complexes with chemistries that allow them to be available in the soil but unavailable to the plant.

Coating a fertilizer with water based products can result in severe clumping of the fertilizer granules during blending, or gelling of the [P(OA)]s due to high electrolyte content caused by the fertilizer granule dissolving into the water. Clumping has a negative impact on its effectiveness to complex with metal cations, and/or it requires a drying step for seed coatings to prevent pre-mature sprouting or the growth of mold and mildew, which ultimately destroys the seeds. The use of aqueous based systems also has a deleterious impact on the urease inhibitor NBPT. The agricultural industry needs a technology that is able to easily, safely, evenly, and economically coat fertilizer granules and seeds with non-aqueous, liquid formulations that contain [P(OA)]s that can form water soluble metal cation complexes and free up bound macronutrients such as phosphorous.

DESCRIPTION OF RELATED ART

To present, multiple products have been developed to try to:

Increase the efficiency of the release of macronutrients, such as phosphorus, from a fertilizer formulation in plant absorbable form, Release nutrients bound in the soil as insoluble salts and complexes Deliver a fertilizer formulation that contains micronutrients in a plant available form.

Develop a coating for seeds:
  that is not water based as high moisture content may be detrimental to the health and viability of the seed
  that can delivered desired micronutrients during the seed's germination
  that can provide a hydrophilic coating that can act as a moisture pump to assist in insuring that the seed does not dry out after distribution on the soil when the external seed coating has begun to deteriorate allowing moisture to penetrate to the coating containing [P(OA)] dispersed in the NOSDS.

The mechanisms of action for the vast majority of these products are similar. When a fertilizer containing phosphorus is applied to the soil, most of the phosphorous is in a water-soluble phosphate ion form, the only form of phosphorus that is readily absorbed by the plant. In the presence of moisture, however, these soluble phosphate anions can form complexes with metal cations such as calcium, magnesium, iron, and aluminum. These salts have very low solubility in water and thus, cannot be readily absorbed by plants. Polymers with negatively charged ions can complex with the metal cations resulting in a freed, water-soluble phosphate anion and with the metal cation in a plant available form. Both the phosphate anion and the [P(OA)] complexed cation are now more readily available to plants for absorption.

Various methods or variations of the above described mechanism are listed in the patents below, which are incorporated by reference in their entireties. These methods have been proposed and developed for the release of nutrients bound in the soil, a delivery system for micronutrients to soil and to seeds and the manufacturing processes to produce the metal cation complexing [P(OA)]s.

Boehmke (U.S. Pat. No. 4,839,461) teaches how to synthesize and use a man-made version of polyaspartic acid and its salts that prevents incrustations formed by the metal ions that are responsible for hard water. Boehmke further discloses that this compound can be used as a fertilizer.

Ashmead (U.S. Pat. No. 4,172,072) discloses the use of protein sources to form metal proteinates, which are in a biologically accepted form. Others reveal carboxylic containing entities either as monomers or as polymers such as Danzig (U.S. Pat. No. 4,799,953), which utilizes polymers of thiolactic acid or thioglycolic acid and thiolactic acid, dithiobispropanoic acid and dithiobisacetic acid, Kinnersley (U.S. Pat. No. 4,813,997), which utilizes glycolic and/or lactic acid, and Young (U.S. Pat. Nos. 4,863,506 and 5,059,241) that disclose that d-lactic acid can promote increased plant growth, increased concentration of chlorophyll, and increase the rate of root formation.

Gill (U.S. Pat. No. 5,047,078) utilized scale inhibiting compounds such as those based on polymers of ethylenically unsaturated carboxylic acids and/or maleic acid/anhydride monomers and/or phosphorous based chelators such as dihydroxy ethylidene diphosphonic acid to make available nutrients bound in the soil as insoluble salts and complexes resulting in increased growth and yields.

Kinnersley (U.S. Pat. Nos. 5,350,735 and 5,593,947) and Koskan (U.S. Pat. Nos. 5,783,523 and 5,814,582) teach using poly (organic) acids like poly (amino acids) such as poly(aspartic) acid to enhance fertilizer uptake and promote plant growth.

Sanders (U.S. Pat. Nos. 6,753,395, 6,756,461, 6,818,039, and 8,043,995) demonstrate that man-made [P(OA)]s based on maleic, itaconic and/or citraconic anhydrides can be utilized to enhance nutrient uptake by plants.

Sanders (U.S. Pat. Nos. 8,016,907 and 8,025,709) show the importance of having a quick drying product that one can apply to the surface of granules for fertilizer. Sanders accomplish this by using 10-50% of a volatile alcohol such as methanol.

Many of these disclosures are now available in the marketplace. A 30% aqueous solution of sodium salt of a maleic-itaconic copolymer, (U.S. Pat. No. 6,515,090, Sanders), is marketed under the brand name Avail. Another polymer containing 40% sodium poly-lysine aqueous solution is marketed as P-Max in the US market. A similar polymer, poly-aspartate, was also used for this purpose (U.S. Pat. No. 5,350,735 to Kinnersley). In the market, a composition that contains 30% aqueous solution of sodium polyaspartate is marketed as X10D (Flexible Solution International). These products have been shown to increase the presence of macronutrients and micronutrients in plant tissue.

However, all these products suffer from the same drawback. Most fertilizers components tend to be solid granules and water soluble. The above-stated patents are almost exclusively based on aqueous solutions and/or they contain >5% water. In many cases, the solid fertilizers applied with a coating of an aqueous solution/dispersion can form agglomerations clogging field application equipment and making it difficult to ensure an even distribution of fertilizer on fields. If these granules of fertilizer have also been coated with a moisture-sensitive urease inhibitor like an alkyl thiophosphoric triamide, the presence of moisture from water based products will result in degradation of these important urease inhibitors, negatively impacting/limiting their performance. Some innovations have to be sold as a costly, separate application product because of the presence of water. While other inventions teach that polymers are dried to form powders and then blended into fertilizer compositions or by binding the [P(OA)] and or its salt to the fertilizer granules through liquid polymers that act as a glue. However, this methodology usually requires drying to remove the binder's solvent to promote [P(OA)] adhesion to the granule surface. Newer technologies utilize volatile organic solvents to promote quick drying, but this approach increases the VOC release and utilizes a low flash point alcohol such as methanol adding an unnecessary flammable hazard to the processing of fertilizer. But of these methods cannot utilize simple equipment such as a blender or mixer to apply a formulation comprising a layer of [P(OA)]s and/or their salts on the surface of solid fertilizer granules, soil and seeds safely, quickly, evenly, and economically.

For coating seeds with micronutrients, many technologies utilize aqueous delivery systems that require an extra drying step. Because of the sensitivity of seeds to heat, most drying is accomplished either with vacuum extraction or through low temperature air flow drying. The drying process is usually slow, can cause seeds to be dried below the moisture levels required for good seed viability and adds cost to seed production. Various methods or variations of the above described mechanism are listed in the patents below, which are incorporated by reference in their entireties.

Barclay (U.S. Pat. No. 5,994,265) reveals seed coating composition including molybdenum (molybdenum trioxide), a sulfur-containing component (gypsum) and an aqueous binder (polyvinyl alcohol) for improving seed and seedling performance. Barclay also recognized the importance of limiting the moisture content of the seeds/coating as to the quality and viability of the seed.

Johnson (U.S. Pat. No. 7,001,869) teach how to produce a coated seed with a treatment based on an aqueous formulation comprising macronutrients, micronutrients, an antimicrobial agent and other additives.

Obert (U.S. Pat. No. 6,557,298) teaches the utility of dry seed coatings and that it helps to avoid the spoilage and premature germination problems associated with use of high water content. However, in practice the application of such powders is accompanied by severe and undesirable dusting during processing and in application.

To address these problems, there is a need for a non-aqueous liquid formulation that can easily, safely, evenly and economically coat fertilizer granules and seeds without resulting in agglomeration during blending and storage. These non-aqueous liquid formulations contain components that will liberate bound nutrients are safe for contact with humans and animals, have low moisture, be environmentally friendly and be applied as a coating to fertilizer and seed utilizing simple blending equipment.

SUMMARY OF THE INVENTION

The present invention is comprised of one or more organic solvents that create a non-aqueous organo solvent delivery system, (NOSDS), and one or more poly(organic acids), [P(OA)]s, and/or their salts that results in a stable, non-aqueous dispersion that can coat fertilizer granules and seeds easily, safely, evenly and economically.

In an embodiment, the present invention provides more flexibility for fertilizer manufacturers and farmers to produce fertilizers designed for a particular soil while including one or more of a NOSDS/[P(OA)]s formulation, nitrification inhibitors, urease inhibitors, pesticides, fungicides, herbicides, insecticides and micronutrients.

In an embodiment, the present invention relates to improving the efficiency of man-made and/or natural organic-based animal manure fertilizers by administration of formulations containing poly(organic acids), [P(OA)]s, and/or their salts dispersed in a Non-aqueous Organic Solvent Delivery System (NOSDS). Utilizing a NOSDS allows for coating all components in a fertilizer formulation including but not limited to Urea, Manure, mono-ammonium phosphate (MAP), di-ammonium phosphate (DAP), solid micronutrients such as lime, zinc chloride, etc.) with a layer of [P(OA)]s and/or their salts that liberates, in a plant available form, the micronutrient metals and macronutrients, that are bound as insoluble salts and complexes in the soil. The carboxylic groups of a [P(OA)] that can exist within the [P(OA)] as carboxylic acids, carboxylic anhydrides and/or carboxylic imides, dispersed within the NOSDS, can be neutralized with one or more metals in the form of elemental metals, metal oxides, metal hydroxides, metal alkylates and metal carbonates and/or nitrogen containing compounds such as ammonia, ammonium hydroxide or organoamines to form a stable dispersion that can contain completely complexed micronutrients and provide the vehicle for the delivery of these nutrients to soils and/or as a coating to the surfaces fertilizer granules and seeds. The metal or metal portions of one of the reactant can further be defined for this invention as Na, K, Mg, Ca, Fe, Zn, Mn, Cu, Co, Mo, Ni. Organoamine is one or more of the group consisting of mono $C_{1-6}$ amine, di $C_{1-6}$ amine, tri $C_{1-6}$ amine, mono ethanol amine, diethanol amine, triethanol amine, monoisopropyl amine, diisopropyl amine, triisopropyl amine, diethyl amine, diethylene triamine, triethyl tetraamine, tetraethyl pentamine. It has also been learned that [P(OA)]s and/or their salts can be produced in situ in a NOSDS utilizing organic acids/esters monomers dispersed/suspended within the NOSDS, heated to a polymerization temperature with or without catalyst and then neutralized/reacted with one or more macronutrients and/or micronutrients. The liquid compositions of [P(OA)]s in a NOSDS and the methods to produce a [P(OA)] within a NOSDS results in a flowable, low moisture liquid that can be readily mixed with liquid fertilizers or applied safely, quickly, evenly and economically on the surface of solid fertilizer granules, soil and seeds.

A salt of a [P(OA)] is defined in this invention as the reaction/neutralization of one or more of the carboxylic groups of a [P(OA)] that can exist within the [P(OA)] as carboxylic acids, carboxylic anhydrides and/or carboxylic imides with one or more metals in the form of elemental metals, metal oxides, metal hydroxides, metal alkylates and metal carbonates and/or with nitrogen containing compounds such as ammonia, ammonium hydroxide or organoamines resulting in a stable dispersion of salts of [P(OA)] in a NOSDS. The metal or metal portions of one of the reactants can further be defined for this invention as Na, K, Mg. Ca, Fe, Zn, Mn, Cu, Co, Mo, and/or Ni. An organoamine is one or more of the group consisting of mono $C_{1-6}$ amine, di $C_{1-6}$ amine, tri $C_{1-6}$ amine, mono ethanol amine, diethanol amine, triethanol amine, monoisopropyl amine, diisopropyl amine, triisopropyl amine, diethyl amine, diethylene triamine, triethyl tetraamine, and tetraethyl pentamine.

In embodiments, the present invention also relates to improved solvent formulations (NOSDS) for [P(OA)]s and/or their salts for application to man-made and/or natural organic based animal manure fertilizers. In a variation, [P(OA)]s may be solid chemical substances, which are dissolved in a suitable NOSDS to allow application at low levels in the field. Additionally, non-aqueous solutions of [P(OA)]s may be desirable when they are to be incorporated as components of a granular mixed fertilizer, such that they can be deposited as a coating in a controlled and homogenous layer. In one embodiment, the [P(OA)]s can be produced in situ utilizing the starting organic acid/ester monomers dispersed/suspended within the NOSDS, heating the formulation to a polymerization temperature, with or without catalysts, and then neutralizing/reacting the formulation with one or more macronutrients and/or micronutrients. The composition can be utilized for coating fertilizer granules and seeds and/or added to liquid fertilizers. In one embodiment, this invention proposes formulations of NOSDS that comprise mixtures containing aprotic and/or protic solvents, which are more environmentally friendly and are safe for manufacturers, transporters and others who work with/handle the compositions/formulations.

In one embodiment, improved liquid delivery formulations have been developed that deliver effective levels of [P(OA)]s and/or their salts that can liberate nutrients bound in the soil as insoluble salts and complexes. It has been found that the liquid delivery formulations of the present invention provide a liquid vehicle, NOSDS, to deliver an even, non-clumping layer of the desired [P(OA)]s and/or their salts to the surfaces of fertilizer granules and/or seeds. These new liquid delivery formulations for [P(OA)]s and/or their salts are non-aqueous organo solvent delivery systems, NOSDSs, that improve the storage life of fertilizers containing urease inhibitors such as alkyl thiophosphoric triamides, acetohydroxamic acid and its derivatives, phosphodiamidates relative to those formulations containing greater than 1% water. In fact, because of the present invention, one can now combine [P(OA)]s and/or their salts, nitrification inhibitors, pesticides, fungicides, herbicides, insecticides and urease inhibitors in one product by either blending together the dispersions of each active ingredient or by combining the pesticides, fungicides, herbicides, insecticides and the nitrification and urease inhibitors in the same improved solvent formulation(s), NOSDS.

In embodiments, the present invention is compositions/formulations of P(OA)]s and/or their salts in a NOSDS that:
Is environmentally safe;
Has flashpoints above 145° F.;
Is inherently rated safe for contact with humans and animals;
Provides stable dispersions of [P(OA)]s or their salts at levels of 1-50% in the NOSDS at storage temperatures down to at least 10° C.;
Provides improved even application of a coating to fertilizer granules and seeds while not causing clumping of the fertilizer granules, premature seed germination and does not support of the growth of mold and mildew on seeds;
Will not detrimentally impact the stability of alkyl thiophosphoric triamides.

In one embodiment, it has been discovered that while various organic solvents might meet some of the above criteria, the delivery system of the present invention can be optimized to provide a formulation with a high concentration of [P(OA)]s and/or their salts while maintaining a low chill point by combining two or more organic solvents as a NOSDS. In one embodiment, one process for preparing the formulations of the present invention is to heat the combined solvents to temperatures 60-100° C. and then charging the [P(OA)]s and/or their salts in a combined level of 10-60% of the total formula composition, which can be dissolved in the NOSDS with moderate agitation.

In one embodiment, the present invention relates to an effective solvent combination that comprises dimethyl sulfoxide (DMSO), which can be used in combination with another liquid organo solvent that has a low chill point and good solvating properties. Besides the advantages listed above, DMSO also has the advantage of potentially serving as a source of the important nutrient sulfur.

DETAILED DESCRIPTION

In an embodiment, the present invention is comprised of one or more organic solvents that create a non-aqueous organo solvent delivery system, (NOSDS), and one or more poly(organic acids), [P(OA)]s, and/or their salts in a stable, non-aqueous dispersion that can coat fertilizer granules and seeds easily, safely, evenly and economically.

A salt of a [P(OA)] is defined in this invention as the neutralization of one or more of the carboxylic (carboxylate) groups of a [P(OA)] that can exist within the [P(OA)] as carboxylic acids, carboxylic anhydrides and/or carboxylic imides with one or more metals in the form of elemental metals, metal oxides, metal hydroxides, metal alkylates and metal carbonates and/or nitrogen containing compounds such as ammonia, ammonium hydroxide or organoamines resulting in a stable dispersion of salts of [P(OA)] in a NOSDS. The metal or metal portions of one of the reactant can further be defined for this invention as Na, K, Mg, Ca, Fe, Zn, Mn, Cu, Co, Mo, and/or Ni. [An organoamine is one or more of the group consisting of mono $C_{1-6}$ amine, di $C_{1-6}$ amine, tri $C_{1-6}$ amine, mono ethanol amine, diethanol amine, triethanol amine, monoisopropyl amine, diisopropyl amine, triisopropyl amine, diethyl amine, diethylene triamine, triethyl tetraamine, and tetraethyl pentamine.

These delivery formulations not only provide a liquid vehicle to deliver an even, non-clumping coating of the desired [P(OA)]s and/or their salts to the surfaces of fertilizer granules and/or seeds, but it has been discovered that formulations based on non-aqueous organo solvent delivery systems, NOSDS, do not negatively impact the storage life of the important urease inhibitors, such as alkyl thiophosphoric triamides (such as NBPT). Alkyl thiophosphoric triamides have been shown to be extremely effective urease inhibitors but if present in combination with an aqueously dispersed [P(OA)] and/or its salt, it will suffer from degradation upon storage if exposed to moisture present in aqueous dispersions. Thus, in one embodiment the present invention relates to compositions that are substantially free of water.

In an embodiment, a stable dispersion of one or more [P(OA)]s and/or their salts in a non-aqueous organo solvent delivery system, NOSDS, can contain and one or more of the following:
Urease inhibitor(s);
Nitrification inhibitor(s);
Pesticides, herbicides, fungicides and insecticides
a food coloring or dye may be used to improve the visual evidence of complete coverage and serve as a visual marker;
scents or masking agents to improve the odor of the formula;
nonionic, anionic, cationic, zwitterionic, and/or amphoteric surfactants to improve formula application performance of fertilizer granules;
buffering agents, micronutrients and/or flow modifiers such as silica, zinc stearate, calcium stearate and the like.

In one embodiment, the improved solvent formulations, NOSDS, of the present invention meet one or more of the following criteria: They:
Are environmentally safe;
Have flashpoints above 145° F.;
Are inherently rated safe for contact with humans and animals;
Provide stable dispersions of [P(OA)]s or their salts at levels of 1-50% within a NOSDS at storage temperatures down to at least 10° C.;
Provide improved even application of a coating to fertilizer granules and seeds while not causing clumping of the fertilizer granules, premature seed germination and does not support of the growth of mold and mildew on seeds;
Will not detrimentally impact the stability of alkyl thiophosphoric triamides.

In one embodiment, a stable non-aqueous, liquid formulation can be produced that comprises a sodium polyaspartate (polymer weight=500 to 10,000 or alternatively about 1000-7500 or alternatively 1500-5000 or alternatively about 1750-3000) and a NOSDS. In an embodiment, the formulations can be made by dissolving the sodium polyaspartate into a NOSDS comprised of one or more of the following a) one or more protic solvents from the group consisting of
1) an alcohol from the family of $C_{1-10}$ alkanols, 2) polyols selected from the group consisting of trimethylol propane, trimethylol ethane, pentaerythritol, sorbitol and sorbitan, glucose, fructose, galactose, and/or glycerin, 3) poly($C_{1-10}$ alkylene) glycols, 4) alkylene glycols selected from the group consisting of ethylene, 1,3 propylene glycol, 1,2 propylene glycol, and/or butylene glycol, 5) isopropylidene glycerol 6) alkylene glycol alkyl ethers selected from the group consisting of tripropylene glycol methyl ether, tripropylene glycol butyl ether, dipropylene glycol butyl ether and/or dipropylene glycol butyl ether, 7) ethyl, propyl, or butyl lactate, 8) an alkanolamine selected from the group consisting of ethanolamine, diethanolamine, dipropanolamine, methyl diethanolamine, monoisopropanolamine and/or triethanolamine and/or 9) glycerol carbonate.

b) and/or one or more aprotic solvents from the group consisting of

1) Dimethyl Sulfoxide and/or 2) dialkyl, diaryl, or alkylaryl sulfoxide(s) having the formula:

$R_1S(O)_xR_2$ wherein $R_1$ and $R_2$ are each independently a $C_{1-6}$ alkylene group, an aryl group, or $C_{1-6}$ alkylenearyl group or $R_1$ and $R_2$ with the sulfur to which they are attached form a 4 to 8 membered ring wherein $R_1$ and $R_2$ together are a $C_{1-6}$ alkylene group which optionally contains one or more atoms selected from the group consisting of O, S, Se, Te, N, and P in the ring and x is 1 or 2.
3) alkylene carbonates selected from the group consisting of ethylene carbonate, propylene carbonate and/or butylene carbonate, 4) polyols capped with acetate or formate wherein the polyol portion may be one or more of ethylene glycol, 1,3 propylene glycol, 1,2 propylene glycol, butylene glycol, trimethylol propane, trimethylol ethane, pentaerythritol, sorbitol and sorbitan, glucose, fructose, galactose and/or glycerin, 5) alkylene glycol alkyl ethers acetates selected from the group consisting of dipropylene glycol methyl ether acetate, tripropylene glycol methyl ether acetate, and/or tripropylene glycol butyl ether acetate and/or, 6) isophorone, 7) dimethylsuccinate, dimethyl adipate, diethyl glutarate, and/or dimethyl glutarate, 8) dimethylacetamide, dimethylformamide, dimethyl-2-imidazolidinone 9) hexamethylphosphoramide, 10) 1,2-dimethyloxethane, 2-methoxyethyl ether, 11) cyclohexylpyrrolidone and/or 12) limonene.

Additionally, the liquid delivery formulations of the present invention may optionally contain one or more of the following:
Urease inhibitor(s);
Nitrification inhibitor(s);
Pesticides, herbicides, fungicides and insecticides
a food coloring or dye may be used to improve the visual evidence of complete coverage and serve as a visual marker;
scents or masking agents to improve the odor of the formula;
nonionic, anionic, cationic, zwitterionic, and/or amphoteric surfactants to improve formula application performance of fertilizer granules;
buffering agents, micronutrients and/or flow modifiers such as silica, zinc stearate, calcium stearate and the like.

In an embodiment, the formulation may contain one or more [P(OA)]s and/or their salts comprised of the following monomers either as homopolymers, copolymers and/or terpolymers at effective levels in the NOSDS wherein they may be present in an amount between about 5-50% of the total amount of the formulation. The [P(OA)]s may be aspartic acid
$C_1$-$C_6$ partial or di-ester of aspartic acid
glutamic acid
$C_1$-$C_6$ partial or di-ester of glutamic acid
maleic anhydride
itaconic anhydride
citraconic anhydride
citric acid
$C_1$-$C_6$ partial or tri-ester of citric acid
acrylic acid
$C_1$-$C_6$ partial or full ester of acrylic acid
methacrylic acid
$C_1$-$C_6$ partial or full ester of methacrylic acid
maleic acid
$C_1$-$C_6$ partial or di-ester of maleic acid
itaconic acid
$C_1$-$C_6$ partial or di-ester of itaconic acid
citraconic acid
$C_1$-$C_6$ partial or di-ester of citraconic acid In an embodiment, an 80/20 to 20/80 mix of dimethyl sulfoxide (DMSO) and ethylene glycol is made and subsequently polyaspartic acid (or its salt or ester) is added with the polyaspartate being about 5-45% by weight of the total composition. In an embodiment, polyaspartate is added, under agitation, to the combined solvents that have been heated in a mixing vessel at a desired temperature of about 0° C. to 150° C., or alternatively at a temperature of about 10° C. to 120° C. or alternatively, at a temperature of about 20° C. to 100° C., or alternatively between about 50° (C and 100° C., and mixed until the polyaspartate acid is completely dissolved. The heated mix vessel, in this embodiment, may be jacketed and the temperature carefully controlled. In an embodiment, the mixing action should allow complete mixing without too much aeration. In a variation, the heating may be accomplished using hot water or low pressure steam to control any hot spots on walls of the vessel to prevent heat degradation. At this stage, the mixture can be cooled to about 35° C. and then the NBPT can be added and agitated until completely dissolved. The mixture can be cooled to 25° C. or below and one or more of the following may be added, if desired:
Urease inhibitor(s);
Nitrification inhibitor(s);
Pesticides, herbicides, fungicides and insecticides
a food coloring or dye may be used to improve the visual evidence of complete coverage and serve as a visual marker;
scents or masking agents to improve the odor of the formula;
nonionic, anionic, cationic, zwitterionic, and/or amphoteric surfactants to improve formula application performance of fertilizer granules;
buffering agents, micronutrients and/or flow modifiers such as silica, zinc stearate, calcium stearate and the like.

It should be recognized that in the temperature ranges given above, the ranges are set so as to allow adequate dissolution of the various compounds. The inventors recognize that should a compound be added that has temperature stability issues, the additions may be under reduced pressure conditions so as to prevent temperature sensitive degradations of the one or more compounds but at the same time allowing their dissolution in the NOSDS.

In an embodiment, a polysuccinimide (PSI) powder (molecular weight of 1000-10,000 may be added at a 5-50% level relative to a composition comprising ethylene glycol under agitation and at a temperature of 60-80° C. The mixture is then heated to 100-180° C. and held until all particles are dissolved. An alkaline or acid catalyst such as KOH or pTSA can be added to improve conversion from PSI to Polyaspartate Poly-EG ester. The batch is then cooled to 50-80° C. In an embodiment, KOH flakes are slowly charged, the temperature is held at 50-100° C. and mixed until all the KOH flakes are dissolved. In an embodiment, the mixing action might include one or more of high shear devices such as a cowles blade, a colloid mill, a rotor stator and/or a ball mill.

In an embodiment, a polysuccinimide (PSI) powder (molecular weight of 3000-5000) may be added at a 5-50% level relative to a composition comprising ethylene glycol under agitation and at a temperature of 60-80° C. The mixture is then heated to 100-180° C. and held until all particles are dissolved and the PSI is converted to a Polyaspartate Poly-EG ester. An alkaline or acid catalyst such as KOH or pTSA can be added to improve conversion from PSI to Polyaspartate Poly-EG ester. The batch is then cooled to 50-80° C. and the EG ester groups are partially saponified with enough of one or more metals in the form of elemental metals, metal oxides, metal hydroxides, metal alkylates and metal carbonates and/or with nitrogen containing compounds such as ammonia, ammonium hydroxide or organoamines to form a stable dispersion within the ethylene glycol. The metal or metal portions of one of the reactant can further be defined for this invention as Na, K, Mg, Ca, Fe, Zn, Mn, Cu, Co, Mo, and/or Ni. An organoamine is one or more of the group consisting of mono $C_{1-6}$ amine, di $C_{1-6}$ amine, tri $C_{1-6}$ amine, mono ethanol amine, diethanol amine, triethanol amine, monoisopropyl amine, diisopropyl amine, triisopropyl amine, diethyl amine, diethylene triamine, triethyl tetraamine, and tetraethyl pentamine.

In an embodiment, the mixing action might include one or more of high shear devices such as a cowles blade, a colloid mill, a rotor stator and/or a ball mill.

In another embodiment, polyaspartate, ammonia salt, may be present at a 10-50% level in a solution mix of DMSO and ethylene glycol at a ratio of about 80/20 to 20/80. In this embodiment, polyaspartate ammonia salt may be added, under agitation to a NOSDS that is a blend of protic and protic solvents that have been heated in a mixing vessel to a desired temperature of about 0° C. to 60° C., or alternatively, to a temperature of about 10° C. to 50° C. and, alternatively, to a temperature of about 20° C. to 40° C. and mixed until the polyaspartate, ammonia salt, is completely dissolved. Also in this embodiment, the heated mix vessel may be jacketed and temperature controlled. In an embodiment, the mixing action may allow complete mixing without too much aeration. In an embodiment the mixing action might include one or more of high shear devices such as a cowles blade, a colloid mill, a rotor stator and/or a ball mill. The heating may be accomplished using hot water and/or low pressure steam to control any hot spots on the walls of the vessel, which can prevent heat degradation. At this stage, the mixture can be cooled to about 25° C. or below and one or more of the following additives may be added, if desired:

Urease inhibitor(s);
Nitrification inhibitor(s);
Pesticides, herbicides, fungicides and insecticides
a food coloring or dye may be used to improve the visual evidence of complete coverage and serve as a visual marker;
scents or masking agents to improve the odor of the formula;
nonionic, anionic, cationic, zwitterionic, and for amphoteric surfactants to improve formula application performance of fertilizer granules;
buffering agents, micronutrients and/or flow modifiers such as silica, zinc stearate, and/or calcium stearate.

In an embodiment, polyaspartate and/or its acid may be added at a 5-50% level relative to a composition comprising ethylene glycol. In this embodiment, polyaspartate acid may be added, under agitation, to the solvent that has been heated in a mixing vessel at a temperature of about 0° C. to 60° C. and mixed until the polyaspartate is completely dissolved. In an embodiment, the heated mix vessel may be jacketed and the temperature controlled. In a variation, the mixing action allows complete mixing without too much aeration. The heating can be accomplished using hot water and/or low pressure steam to control any hot spots on the walls of the vessel to prevent heat degradation. At this stage, the mixture may be cooled to 25° C. or below and one or more of the following may be added, if desired:

Urease inhibitor(s);
Nitrification inhibitor(s);
Pesticides, herbicides, fungicides and insecticides
a food coloring or dye may be used to improve the visual evidence of complete coverage and serve as a visual marker;
scents or masking agents to improve the odor of the formula;
nonionic, anionic, cationic, zwitterionic, and/or amphoteric surfactants to improve formula application performance of fertilizer granules;
buffering agents, micronutrients and/or flow modifiers such as silica, zinc stearate, and/or calcium stearate.

In an embodiment, polyaspartate ammonia salt may be incorporated at a 5-50% level relative to the amount of ethylene glycol. In this embodiment, polyaspartate ammonia may be added, under agitation, to the protic solvent that has been heated in a mixing vessel at a temperature of about 0° C. to 60° C. and mixed until the polyaspartate ammonia salts are completely dissolved. The heated mix vessel may be jacketed and the temperature controlled. In a variation, the mixing action allows complete mixing without too much aeration. The heating can be accomplished using hot water or low pressure steam to control any hot spots on the walls of the vessel to prevent heat degradation. In a variation, the mixing action might include one or more of high shear devices such as a cowles blade, a colloid mill, a rotor stator and/or a ball mill. At this stage, the mixture may be cooled to 25° C. or below and one or more of the following may be added, if desired:

Urease inhibitor(s);
Nitrification inhibitor(s);
Pesticides, herbicides, fungicides and insecticides
a food coloring or dye may be used to improve the visual evidence of complete coverage and serve as a visual marker;
scents or masking agents to improve the odor of the formula;
nonionic, anionic, cationic, zwitterionic, and/or amphoteric surfactants to improve formula application performance of fertilizer granules;
buffering agents, micronutrients and/or flow modifiers such as silica, zinc stearate, and/or calcium stearate.

In an embodiment, polymaleic anhydride may be produced in a solvent such as xylene utilizing an organic peroxide as a catalyst and using a process known to those of skill in the art. The resulting solvated poly (organic acid) can undergo solvent replacement by charging an aprotic NOSDS comprised of one or more of 1) Dimethyl Sulfoxide and/or 2) dialkyl, diaryl, or alkylaryl sulfoxide(s) having the formula:

wherein $R_1$ and $R_2$ are each independently a $C_{1-6}$ alkylene group, an aryl group, or $C_{1-6}$ alkylenearyl group or $R_1$ and $R_2$ with the sulfur to which they are attached form a 4 to 8 membered ring wherein $R_1$ and $R_2$ together are a $C_{1-6}$ alkylene group which optionally contains one or more atoms selected from the group consisting of O, S, Sc, Te, N, and P in the ring and x is 1 or 2.

3) alkylene carbonates selected from the group consisting of ethylene carbonate, propylene carbonate and/or butylene carbonate, 4) polyols capped with acetate or formate wherein the polyol portion may be one or more of ethylene glycol, 1,3 propylene glycol, 1,2 propylene glycol, butylene glycol, trimethylol propane, trimethylol ethane, pentaerythritol, sorbitol and sorbitan, glucose, fructose, galactose and/or glycerin, 5) alkylene glycol alkyl ethers acetates selected from the group consisting of dipropylene glycol methyl ether acetate, tripropylene glycol methyl ether acetate, and tripropylene glycol butyl ether acetate and/or, 6) isophorone, 7) dimethylsuccinate, dimethyl adipate, diethyl glutarate, and/or dimethyl glutarate, 8) dimethylacetamide, dimethylformamide, dimethyl-2-imidazolidinone 9) hexamethylphosphoramide, 10) 1,2-dimethyloxethane, 2-methoxyethyl ether, 11) cyclohexylpyrrolidone and/or 12) limonene.

One may then begin to strip the unwanted solvent out either by differential boiling points or by the use of a vacuum (such as by use of a rotary evaporator) until the unwanted solvent is reduced to a level that is less than about 1%. The polymaleic anhydride can be neutralized within the NOSDS to a desired pH with one or more metals in the form of elemental metals, metal oxides, metal hydroxides, metal alkylates and metal carbonates and/or with nitrogen containing compounds such as ammonia, ammonium hydroxide or organoamines resulting in a stable dispersion of salts of [P(OA)] in a NOSDS. The metal or metal portions of the reactants can further be defined as Na, K, Mg, Ca, Fe. Zn, Mn, Cu, Co, Mo and Ni or mixture thereof. Organoamine is one or more of the group consisting of mono $C_{1-6}$ amine, di $C_{1-6}$ amine, tri $C_{1-6}$ amine, mono ethanol amine, diethanol amine, triethanol amine, monoisopropyl amine, diisopropyl amine, triisopropyl amine, diethyl amine, diethylene triamine, triethyl tetraamine, tetraethyl pentamine.

If water results from neutralization or from the addition of aqueous solutions of these alkalis, the water can be removed by stripping (such as by use of a rotary evaporator) through temperature or through lower temperature/vacuum to ensure a low moisture formula. Other known means of removing water can be used such as by use of molecular sieves or by addition of a drying agent (such as $Na_2SO_4$ or $MgSO_4$) and subsequent filtration.

In an embodiment, potassium polyaspartate can be incorporated in amounts that are about 10-45% of a formulation mixture that also contains ethylene and propylene glycol at ratios from about 80/20 to 20/80. In an embodiment, potassium polyaspartate may be added, under agitation, to the combined solvents that have been heated in a mixing vessel at a temperature of about 0° C. to 150° C., or alternatively to a temperature of about 20° C. to 130° C., or alternatively to a temperature of about 40° C. to 120° C., or alternatively to a temperature of about 50° C. to 100° C., and mixed until the potassium polyaspartate is completely dissolved. In an embodiment, the heated mix vessel may be jacketed and the temperature carefully controlled. In a variation, the mixing action allows complete mixing without too much aeration. Heating can be accomplished using hot water or low pressure steam to control any hot spots on the walls of the vessel to prevent heat degradation to the potassium polyaspartate. Alternatively, the mixing may be done at reduced pressure, the action can be performed in an inert atmosphere (such as but not limited to nitrogen, argon and/or carbon dioxide) to limit thermal or oxidative degradation and/or the mixing action might include one or more of high shear devices such as a cowles blade, a colloid mill, a rotor stator and/or a ball mill. At this stage (after the initial mixing), the mixture may be cooled to about 25° C. or below and one or more of the following may be added, if desired:

Urease inhibitor(s);
Nitrification inhibitor(s);
Pesticides, herbicides, fungicides and insecticides
a food coloring or dye may be used to improve the visual evidence of complete coverage and serve as a visual marker;
scents or masking agents to improve the odor of the formula;
nonionic, anionic, cationic, zwitterionic, and/or amphoteric surfactants to improve formula application performance of fertilizer granules;
buffering agents, micronutrients and/or flow modifiers such as silica, zinc stearate, and/or calcium stearate.

In another variation, the mixture of [P(OA)]s in NOSDS can be placed under high shear agitation such as but not limited to an overhead agitator equipped with a cowles blade or a rotor stator mixer to assist in reducing viscosity of the mixture. In an embodiment, the present invention relates to making a stable non-aqueous dispersion of a polyaspartate salt in a NOSDS. In a variation a polysuccinimide is heated to 100-160° C. in the presence of an excess of a protic NOSDS resulting in the formation of a polyaspartate-ester dispersed in the protic NOSDS which is subsequently saponified with one or more metals in the form of elemental metals, metal oxides, metal hydroxides, metal alkylates and metal carbonates and/or with nitrogen containing compounds such as ammonia, ammonium hydroxide or organoamines resulting in a stable dispersion of salts of [P(OA)] in a NOSDS. The metal or metal portions of the reactants can further be defined as Na, K, Mg, Ca, Fe, Zn, Mn, Cu, Co, Mo and Ni. An organoamine is one or more of the group consisting of mono $C_{1-6}$ amine, di $C_{1-6}$ amine, tri $C_{1-6}$ amine, mono ethanol amine, diethanol amine, triethanol amine, monoisopropyl amine, diisopropyl amine, triisopropyl amine, diethyl amine, diethylene triamine, triethyl tetraamine, and tetraethyl pentamine. In a variation, protic and/or aprotic solvent(s) can be added to the freed protic solvent to give the composition the desired coating properties.

In an embodiment, the present invention relates to making the liquid compositions that can be readily mixed with liquid fertilizers or applied safely, quickly, evenly and economically on the surface of solid fertilizer granules, soil and seeds. In a variation, a polysuccinimide is heated to 100-160° C. in the presence of an excess of a protic solvent resulting in the formation of a polyaspartate-ester dispersed in the protic solvent which is subsequently reacted with oxides, hydroxides & carbonates of zinc, calcium, magnesium, iron, manganese, copper, cobalt, and/or nickel resulting in a stable dispersion of micronutrient salts of polyaspartic acid ester in NOSDS. In a variation the micronutrient salts of polyaspartic acid ester in NOSDS can be fully neutralized with one or more metals in the form of elemental metals, metal oxides, metal hydroxides, metal alkylates and metal carbonates and/or with nitrogen containing compounds such as ammonia, ammonium hydroxide or organoamines resulting in a stable dispersion of salts of [P(OA)] in a NOSDS. The metal or metal portions of the reactants can further be defined as Na, K, Mg, Ca, Fe, Zn, Mn, Cu, Co, Mo and Ni. An organoamine is one or more of the group consisting of mono $C_{1-6}$ amine, di $C_{1-6}$ amine, tri $C_{1-6}$ amine, mono ethanol amine, diethanol amine, triethanol amine, monoisopropyl amine, diisopropyl amine, triisopropyl amine, diethyl amine, diethylene triamine, triethyl tetraamine, and/or tetraethyl pentamine. The NOSDS is free to become a component of the composition's organo solvent system. In a variation, the complexed micronutrients have also been shown to have urease inhibition performance and thus can act both as a micronutrient and as a urease inhibitor.

In an embodiment, the present invention relates to making the liquid compositions that can be readily mixed with liquid fertilizers or applied safely, quickly, evenly and economically on the surface of solid fertilizer granules, soil and seeds. In a variation, a polysuccinimide is heated to 40-80° C. in the presence of an aprotic NOSDS and mixed until the polysuccinimide is completely dissolved. This dispersed [P(OA)] can be partially or fully neutralized with one or more metals in the form of elemental metals, metal oxides, metal hydroxides, metal alkylates and metal carbonates and/or with nitrogen containing compounds such as ammonia, ammonium hydroxide or organoamines resulting in a stable dispersion of salts of [P(OA)] in a NOSDS. The metal or metal portions of the reactants can further be defined as Na, K. Mg, Ca, Fe, Zn, Mn, Cu, Co, Mo, and Ni. An organoamine is one or more of the group consisting of mono $C_{1-6}$ amine, di $C_{1-6}$ amine, tri $C_{1-6}$ amine, mono ethanol amine, diethanol amine, triethanol amine, monoisopropyl amine, diisopropyl amine, triisopropyl amine, diethyl amine, diethylene triamine, triethyl tetraamine, and/or tetraethyl pentamine. The reaction vessel can be placed under vacuum to remove any residual water formed or introduced.

In an embodiment, the present invention relates to making the liquid compositions that can be readily mixed with liquid fertilizers or applied safely, quickly, evenly and economically on the surface of solid fertilizer granules, soil and seeds. In a variation, a reactive monomer or a blend of reactive monomers such as but not limited to aspartic acid and/or glutamic acid is heated to 100-185° C. in the presence of a molar excess of protic NOSDS resulting in the formation of a poly (organic-ester) which is subsequently saponified, freeing the NOSDS to become a component of the organo solvent system, with one or more metals in the form of elemental metals, metal oxides, metal hydroxides, metal alkylates and metal carbonates and/or with nitrogen containing compounds such as ammonia, ammonium hydroxide or organoamines resulting in a stable dispersion of salts of [P(OA)] in a NOSDS. The metal or metal portions of the reactants can further be defined as Na, K, Mg, Ca, Fe, Zn, Mn, Cu, Co, Mo and Ni. An organoamine is one or more of the group consisting of mono $C_{1-6}$ amine, di $C_{1-6}$ amine, tri $C_{1-6}$ amine, mono ethanol amine, diethanol amine, triethanol amine, monoisopropyl amine, diisopropyl amine, triisopropyl amine, diethyl amine, diethylene triamine, triethyl tetraamine, and/or tetraethyl pentamine. In a variation the molar ratio of the NOSDS to reactive monomer is 1.2 to 1. In another variation, the molar ratio of the NOSDS to reactive monomer is 6 to 1. In another variation the molar ratio of the NOSDS to reactive monomer is 2 to 1. In another variation, the molar ratio of the NOSDS to reactive monomer is 10 to 1. In one variation, the molar ratio may be any ratio between about 0.5 to 1 and 10 to 1. In a variation, the weight ratio of the NOSDS to reactive monomer is 10% to 90%. In another variation, the weight ratio of the NOSDS to reactive monomer is 90% to 10%.

In an embodiment, the present invention relates to making the liquid compositions that can be readily mixed with liquid fertilizers or applied safely, quickly, evenly and economically on the surface of solid fertilizer granules, soil and seeds. In a variation, a reactive monomer or a blend of reactive monomers such as but not limited to acrylic acid, maleic anhydride, maleic acid, citraconic anhydride itaconic anhydride and/or itaconic acid is heated to 60-140° C. in the presence of a molar excess protic NOSDS and with a free radical catalyst such as but not limited to ammonium persulfate, benzoyl peroxide and/or di-tert butyl peroxide resulting in the formation of a poly (organic-ester) which is subsequently saponified, freeing the NOSDS to become a component of the organo solvent system, with one or more metals in the form of elemental metals, metal oxides, metal hydroxides, metal alkylates and metal carbonates and/or with nitrogen containing compounds such as ammonia, ammonium hydroxide or organoamines resulting in a stable dispersion of salts of [P(OA)] in a NOSDS. The metal or metal portions of the reactants can further be defined as Na, K, Mg, Ca, Fe, Zn, Mn, Cu, Co. Mo and Ni. An organoamine is one or more of the group consisting of mono $C_{1-6}$ amine, di $C_{1-6}$ amine, tri $C_{1-6}$ amine, mono ethanol amine, diethanol amine, triethanol amine, monoisopropyl amine, diisopropyl amine, triisopropyl amine, diethyl amine, diethylene triamine, triethyl tetraamine, and/or tetraethyl pentamine.

In a variation, the molar ratio of the NOSDS to reactive monomer is 1.2 to 1. In another variation, the molar ratio of the NOSDS to reactive monomer is 6 to 1. In another variation the molar ratio of the NOSDS to reactive monomer is 2 to 1. In another variation, the molar ratio of the NOSDS to reactive monomer is 10 to 1. In one variation, the molar ratio may be any ratio between about 0.5 to 1 and 10 to 1.

In a variation, the weight ratio of the NOSDS to reactive monomer is 10% to 90%. In another variation, the weight ratio of the NOSDS to reactive monomer is 90% to 10%.

In an embodiment, polyacrylic acid may be produced in a solvent such as methyl ethyl ketone using a peroxide catalyst and a process known to those experienced in the art. The resulting solvated poly (organic acid) can undergo solvent replacement by charging an aprotic NOSDS comprised of one or more of 1) Dimethyl Sulfoxide and/or 2) dialkyl, diaryl, or alkylaryl sulfoxide(s) having the formula:

$R_1S(O)_xR_2$ wherein $R_1$ and $R_2$ are each independently a $C_{1-6}$ alkylene group, an aryl group, or $C_{1-6}$ alkylenearyl group or $R_1$ and $R_2$ with the sulfur to which they are attached form a 4 to 8 membered ring wherein $R_1$ and $R_2$ together are a $C_{1-6}$ alkylene group which optionally contains one or more atoms selected from the group consisting of O, S, Se, Te, N, and P in the ring and x is 1 or 2.

and/or 3) alkylene carbonates such as ethylene carbonate, propylene carbonate and/or butylene carbonate and for 4) polyols capped with acetate or formate wherein the polyol portion may be one or more of ethylene glycol, 1,3 propylene glycol, 1,2 propylene glycol, butylene glycol, trimethylol, propane trimethylol ethane, pentaerythritol, sorbitol and sorbitan, glucose, fructose, galactose and/or glycerin 5) alkylene glycol alkyl ethers acetates such as tripropylene glycol methyl ether acetate, tripropylene glycol butyl ether acetate and/or 6) isophorone 7) dimethylsuccinate, dimethyl adipate, diethyl glutarate, and/or dimethyl glutarate, 8) dimethylacetamide, dimethylformamide, dimethyl-2-imidazolidinone 9) hexamethylphosphoramide, 10) 1,2-dimethyloxethane, 2-methoxyethyl ether, 11) cyclohexylpyrrolidone, and/or 12) limonene.

Subsequently, one can then begin to strip the unwanted solvent out either by differential boiling points or by the use of vacuum until the unwanted solvent is reduced to a level that is less than about 1%. The polyacrylic acid can be neutralized in the new NOSDS to a desired pH with one or more metals in the form of elemental metals, metal oxides, metal hydroxides, metal alkylates and metal carbonates and/or with nitrogen containing compounds such as ammonia, ammonium hydroxide or organoamines resulting in a stable dispersion of salts of [P(OA)] in a NOSDS. The metal or metal portions of the reactants can further be defined as Na, K, Mg, Ca, Fe, Zn, Mn. Cu, Co, Mo and Ni. A organoamine is one or more of the group consisting of mono $C_{1-6}$ amine, di $C_{1-6}$ amine, tri $C_{1-6}$ amine, mono ethanol amine, diethanol amine, triethanol amine, monoisopropyl amine, diisopropyl amine, triisopropyl amine, diethyl amine, diethylene triamine, triethyl tetraamine, and/or tetraethyl pentamine. If water resulting from neutralization or from the addition of aqueous solutions of these alkalis is present, the water can be removed by stripping (such as by use of a rotary evaporator) through temperature or through lower temperature/vacuum to insure a low moisture formula. Alternatively, molecular sieves or drying agents and filtration may be used.

In an embodiment, one or more additional urease inhibitors, one or more additional [P(OA)]s and/or one or more additional nitrification inhibitors may be added to formulations of the present invention. In an embodiment, the additional urease inhibitor, [P(OA)]s and/or nitrification inhibitors may be dissolved in the mixture. In an embodiment, useful mixtures may be prepared either by dilution or mixture with liquid fertilizers.

Examples of the present formulation include adding the liquid invention to an aqueous mixture of urea and ammonium nitrate (UAN) or coating with the liquid invention by contacting the mixture with solid fertilizers components such as formulation including but not limited to Urea, Manure, mono-ammonium phosphate (MAP), di-ammonium phosphate (DAP), solid micronutrients such as lime, zinc chloride, etc). In an embodiment, coated granular fertilizer can be prepared by using any commercially available equipment in which granular product can be mixed or sprayed with the liquid invention. A flow aid, silicas or surfactants such as soap or nonionic surfactants may be added prior to addition of the liquid for improved dispersability.

In an embodiment, the resulting coated fertilizer can be applied to soil in either a liquid and/or a granular form to provide improved nutrient retention in the soil for uptake for plant life.

In an embodiment, the active ingredients are comprised of one or more nitrification inhibitors, one or more urease inhibitors, one or more pesticides, one or more fungicides, one or more herbicides and/or one or more insecticides dispersed within a stable liquid formulation comprised of a one or more polyaspartic acid and/or its salts and a NOSDS (such as the ones described herein).

In an embodiment, the composition may comprise one or more of surfactants, buffers, fragrance/odor masking agents, colorants, micro-nutrients, pesticides, fungicides, herbicides, insecticides and/or flow modifiers.

In an embodiment, the composition is substantially free of water.

In an embodiment, the present invention relates to fertilizer additives. In one embodiment, the fertilizer additive comprises one or more nitrification inhibitors, one or more pesticides, one or more fungicides, one or more herbicides, one or more insecticides and one or more urease inhibitors within a stable liquid formulation comprised of a one or more [P(OA)]s and/or their salts and a NOSDS.

In an embodiment, the present invention relates to fertilizer or seed additives that comprises one or more of the following:
a) one or more fungicides such as but not limited to azoxystrobin, *bacillus lichenformis*, boscalid, captan, chloroneb, chlorothalonil, ethazole (etridiazole), fenarimol, fludioxonil, flutolanil, fosetyl-aluminum, iprodione, mancozeb, mefenoxam, myclobutanil, potassium phosphite, polyoxin D, propamocarb, propiconazole, pyraclostrobin, tebuconazole, thiophanate-methyl, thiram, triadimefon, trifloxystrobin, vinclozolin;
b) one or more herbicides such as but not limited to 2,4-D, 2,4-DB, acetochlor, acifluorfen, alachlor, ametryn, atrazine, aminopyralid, benefin, bensulfuron, bensulide, bentazon, bromacil, bromoxynil, butylate, carfentrazone, chlorimuron, chlorsulfuron, clcthodim, clomazonc, clopyralid, cloransulam, cycloate, DCPA, desmedipham, dicamba, dichiobenil, diclofop, diclosulam, diflufenzopyr, dimethenamid, diquat, diuron, DSMA, endothall, EPTC, ethalfluralin, ethofumesate, fenoxaprop, fluazifop-P, flucarbazone, flufenacet, flumetsulam, flumiclorac, flumioxazin, fluometuron, fluroxypyr, fomesafen, foramsulfuron, glufosinate, glyphosate, halosulfuron, hexazinone, imazamethabenz, imazamox, imazapic, imazaquin, imazethapyr, isoxaben, isoxaflutole, lactofen, linuron, MCPA, MCPB, mesotrione, metolachlor-s, metribuzin, metsulfuron, molinate, MSMA, napropamide, naptalam, nicosulfuron, norflurazon, oryzalin, oxadiazon, oxyfluorfen, paraquat, pelargonic acid, pendimethalin, phenmedipham, picloram, primisulfuron, prodiamine, prometryn, pronamide, propanil, prosulfuron, pyrazon, pyrithiobac, quinclorac, quizalofop, rimsulfuron, sethoxydim, siduron, simazine, sulfentrazone, sulfometuron, sulfosulfuron, tebuthiuron, terbacil, thiazopyr, thifensulfuron, thiobencarb, tralkoxydim, triallate, triasulfuron, tribenuron, triclopyr, trifluralin, triflusulfuron;
c) and/or one or more insecticides such as but not limited to bifenthrin, cypermethrin, permethrin, piperonyl butoxide, lambda-cyhalothrin, (s)-methoprene, deltamethrin, permethrin, esfenvalerate, pyriproxyfen, fipronil, etofenprox, cyphenothrin, carbofuran, chlorpoyrifos, disulfoton, fenvalerate, ethoprop, fonofos, malathion, permethrin, phorate, tefluthrin, terbufos, trimethacarb, allicin, anabasine, azadirachtin, carvacrol, d-limonene, matrine, nicotine, nomicotine, oxymatrine, pyrethrins, cinerins, jasmolin, quassia, rhodojaponin, rotenone, ryania, sabadilla, sanguinarine, triptolide, carbamate insecticides, benzofuranyl methylcarbamate insecticides, dimethylcarbamate insecticides, oxime carbamate insecticides, phenyl methylcarbamate insecticides, dinosam, DNOC, fluorine insecticides, formamidine insecticides, amitraz, chlordimeform, formetanate, formparanate, medimeform, semiamitraz;

within a stable liquid formulation comprised of a one or more [P(OA)]s and/or their salts and a NOSDS. In a variation, one or more nitrification inhibitors, one or more urease inhibitors can be added to the stable liquid formulation.

In an embodiment, the present invention relates to seed additives. In one embodiment, the seed additive comprises one or more nitrification inhibitors, pesticides, fungicides, herbicides, insecticides and one or more urease inhibitors within a stable liquid formulation comprised of a one or more [P(OA)]s and/or their salts and a NOSDS In an embodiment, the present invention relates to making compositions and fertilizer and/or seed additives. In one embodiment, the present invention relates to a method of making a composition to be added to a fertilizer and/or seeds, wherein the method comprises:

heating a mixture comprising one or more [P(OA)] and/or its salt in a NOSDS;

cooling the mixture to a temperature that optionally allows addition of one or more of surfactants, buffers, fragrance/odor masking agents, colorants, micro-nutrients, pesticides, fungicides, herbicides, insecticides and/or flow modifiers.

In one variation of the method, the method comprises further adding the composition to a fertilizer and/or seeds.

In an embodiment, a stable liquid formulation composition comprising one or more [P(OA)]s and/or their salts in a protic NOSDS wherein the protic NOSDS is comprised of one or more of 1) an alcohol from the family of $C_{1-10}$ alkanols, 2) polyols selected from the group consisting of trimethylol propane, trimethylol ethane, pentaerythritol, sorbitol and sorbitan, glucose, fructose, galactose, and glycerin, 3) poly($C_{1-10}$ alkylene) glycols, 4) alkylene glycols selected from the group consisting of ethylene, 1,3 propylene glycol, 1,2 propylene glycol, and butylene glycol, 5) isopropylidene glycerol 6) alkylene glycol alkyl ethers selected from the group consisting of tripropylene glycol methyl ether, tripropylene glycol butyl ether, dipropylene glycol butyl ether and dipropylene glycol butyl ether, 7) ethyl, propyl, or butyl lactate, 8) an alkanolamine selected from the group consisting of ethanolamine, diethanolamine, dipropanolamine, methyl diethanolamine, monoisopropanolamine and triethanolamine and/or 9) glycerol carbonate.

In an embodiment, the formulation may contain one or more [P(OA)]s and/or their salts comprised of the following monomers either as homopolymers, copolymers and/or terpolymers at effective levels in the NOSDS wherein they may be present in an amount between about 5-50% of the total amount:

aspartic acid
$C_1$-$C_6$ partial or di-ester of aspartic acid
glutamic acid
$C_1$-$C_6$ partial or di-ester of glutamic acid
maleic anhydride
itaconic anhydride
citraconic anhydride
citric acid
$C_1$-$C_6$ partial or tri-ester of citric acid
acrylic acid
$C_1$-$C_6$ partial or full ester of acrylic acid
methacrylic acid
$C_1$-$C_6$ partial or full ester of methacrylic acid
maleic acid
$C_1$-$C_6$ partial or di-ester of maleic acid
itaconic acid
$C_{1-6}$ partial or di-ester of itaconic acid
citraconic acid, and/or
$C_1$-$C_6$ partial or di-ester of citraconic acid In a variation, the composition may contain a protic NOSDS from the group that is comprised of one or more of ethylene glycol, propylene glycol, butylene glycol, glycerin, tripropylene glycol and/or their methyl ethers.

In a variation, the one or more protic NOSDS comprise between about 90/10 to 10/90 of the composition.

In a variation, the one or more [P(OA)] and or their salts is potassium aspartate in a formulation wherein potassium aspartate is present in an amount that is between about 10-45% of a total formulation amount and the formulation also contains a mixture of ethylene glycol and propylene glycol in ratios that are between about 20/80 to 80/20.

In an embodiment, the composition may further comprise one or more of surfactants, buffers, fragrance/odor masking agents, colorants, micro-nutrients, dispersed urease inhibitor(s), dispersed nitrification inhibitor(s), dispersed pesticides, dispersed fungicides, dispersed herbicides, dispersed insecticides and/or flow modifiers.

In a variation, the composition is substantially free of water.

In an embodiment, a composition comprising a stable dispersion of one or more [P(OA)]s and/or their salts in a NOSDS comprised of a) one or more protic solvents selected from the group consisting of 1) an alcohol from the family of $C_{1-10}$ alkanols, 2) polyols selected from the group consisting of trimethylol propane, trimethylol ethane, pentaerythritol, sorbitol and sorbitan, glucose, fructose, galactose, and/or glycerin, 3) poly($C_{1-10}$ alkylene) glycols, 4) alkylene glycols selected from the group consisting of ethylene, 1,3 propylene glycol, 1,2 propylene glycol, and/or butylene glycol, 5) isopropylidene glycerol 6) alkylene glycol alkyl ethers selected from the group consisting of tripropylene glycol methyl ether, tripropylene glycol butyl ether, dipropylene glycol butyl ether and/or dipropylene glycol butyl ether, 7) ethyl, propyl, or butyl lactate, 8) an alkanolamine selected from the group consisting of ethanolamine, diethanolamine, dipropanolamine, methyl diethanolamine, monoisopropanolamine and/or triethanolamine and/or 9) glycerol carbonate.

b) and/or one or more aprotic solvent from the group consisting of 1) Dimethyl Sulfoxide and/or 2) dialkyl, diaryl, or alkylaryl sulfoxide(s) having the formula:

wherein $R_1$ and $R_2$ are each independently a $C_{1-6}$ alkylene group, an aryl group, or $C_{1-6}$ alkylenearyl group or $R_1$ and $R_2$ with the sulfur to which they are attached form a 4 to 8 membered ring wherein $R_1$ and $R_2$ together are a $C_{1-6}$ alkylene group which optionally contains one or more atoms selected from the group consisting of O, S, Se, Te, N, and P in the ring and x is 1 or 2.

3) alkylene carbonates selected from the group consisting of ethylene carbonate, propylene carbonate and/or butylene carbonate, 4) polyols capped with acetate or formate wherein the polyol portion may be one or more of ethylene glycol, 1,3 propylene glycol, 1,2 propylene glycol, butylene glycol, trimethylol propane, trimethylol ethane, pentaerythritol, sorbitol and sorbitan, glucose, fructose, galactose and/or glycerin, 5) alkylene glycol alkyl ethers acetates selected from the group consisting of dipropylene glycol methyl ether acetate, triprupylene glycol methyl ether acetate, and/or tripropylene glycol butyl ether acetate and/or, 6) isophorone, 7) dimethylsuccinate, dimethyl adipate, diethyl glutarate, and/or dimethyl glutarate, 8) dimethylacetamide, dimethylformamide, dimethyl-2-imidazolidinone 9) hexamethylphosphoramide, 10) 1,2-dimethyloxethane, 2-methoxyethyl ether, 11) cyclohexylpyrrolidone and/or 12) limonene.

In a variation, the composition may contain one or more [P(OA)]s and/or their salts comprised of the following monomers either as homopolymers, copolymers and/or terpolymers at effective levels in the NOSDS wherein they may be present in an amount between about 5-50% of the total amount:
  aspartic acid
  $C_1$-$C_6$ partial or di-ester of aspartic acid
  glutamic acid
  $C_1$-$C_6$ partial or di-ester of glutamic acid
  maleic anhydride
  itaconic anhydride
  citraconic anhydride
  citric acid
  $C_1$-$C_6$ partial or tri-ester of citric acid
  acrylic acid
  $C_1$-$C_6$ partial or full ester of acrylic acid
  methacrylic acid
  $C_1$-$C_6$ partial or full ester of methacrylic acid
  maleic acid
  $C_1$-$C_6$ partial or di-ester of maleic acid
  itaconic acid
  $C_1$-$C_6$ partial or di-ester of itaconic acid
  citraconic acid
  $C_1$-$C_6$ partial or di-ester of citraconic acid In an embodiment, the composition may contain a protic NOSDS which comprises one or more of the following: ethylene glycol, propylene glycol, butylene glycol, glycerin, tripropylene glycol methyl ether In a variation, an aprotic NOSDS which comprises one or more of the following: dimethyl sulfoxide, propylene carbonate, dimethylsuccinate, diethyl glutarate, or dimethyl glutarate.

In a variation, the ratio of protic NOSDS to aprotic NOSDS is between about 90/10 to 10/90% and a total of the solvating system is between about 10 to 90% of a final composition.

In a variation, the one or more [P(OA)]s and/or their salts comprise sodium aspartate in a formulation wherein sodium aspartate is present in an amount that is between about 10-45% of a total formulation amount and the formulation also contains a) ethylene glycol and/or propylene glycol and b) propylene carbonate in a ratio that is between about 20/80 to 80/20.

In a variation, the composition is substantially free of water.

In an embodiment, the present invention relates to a stable liquid fertilizer and/or seed additive, which comprises one or more [P(OA)]s and/or their salts in a NOSDS comprised of one or more of a) protic solvents from the group consisting of 1) an alcohol from the family of $C_{1-10}$ alkanols, 2) polyols selected from the group consisting of trimethylol propane, trimethylol ethane, pentaerythritol, sorbitol and sorbitan, glucose, fructose, galactose, and/or glycerin, 3) poly($C_{1-10}$ alkylene) glycols, 4) alkylene glycols selected from the group consisting of ethylene, 1,3 propylene glycol, 1,2 propylene glycol, and/or butylene glycol, 5) isopropylidene glycerol 6) alkylene glycol alkyl ethers selected from the group consisting of tripropylene glycol methyl ether, tripropylene glycol butyl ether, dipropylene glycol butyl ether and/or dipropylene glycol butyl ether, 7) ethyl, propyl, or butyl lactate, 8) an alkanolamine selected from the group consisting of ethanolamine, diethanolamine, dipropanolamine, methyl diethanolamine, monoisopropanolamine and/or triethanolamine and/or 9) glycerol carbonate.

b) and/or one or more aprotic solvents from the group consisting of 1) Dimethyl Sulfoxide and/or 2) dialkyl, diaryl, or alkylaryl sulfoxide(s) having the formula:

$$R_1S(O)_xR_2$$

wherein $R_1$ and $R_2$ are each independently a $C_{1-6}$ alkylene group, an aryl group, or $C_{1-6}$ alkylenearyl group or R and R with the sulfur to which they are attached form a 4 to 8 membered ring wherein R and R together are a $C_{1-6}$ alkylene group which optionally contains one or more atoms selected from the group consisting of O, S, Se, Te, N, and P in the ring and x is 1 or 2.

3) alkylene carbonates selected from the group consisting of ethylene carbonate, propylene carbonate and/or butylene carbonate, 4) polyols capped with acetate or formate wherein the polyol portion may be one or more of ethylene glycol, 1,3 propylene glycol, 1.2 propylene glycol, butylene glycol, trimethylol propane, trimethylol ethane, pentaerythritol, sorbitol and sorbitan, glucose, fructose, galactose and/or glycerin, 5) alkylene glycol alkyl ethers acetates selected from the group consisting of dipropylene glycol methyl ether acetate, tripropylene glycol methyl ether acetate, and/or tripropylene glycol butyl ether acetate and/or, 6) isophorone, 7) dimethylsuccinate, dimethyl adipate, diethyl glutarate, and/or dimethyl glutarate, 8) dimethylacetamide, dimethylformamide, dimethyl-2-imidazolidinone 9) hexamethylphosphoramide, 10) 1,2-dimethyloxethane, 2-methoxyethyl ether, 11) cyclohexylpyrrolidone and/or 12) limonene.

In a variation, the fertilizer and/or seed additive may contain one or more [P(OA)]s and/or their salts comprised of the following monomers as homopolymers, copolymers and/or terpolymers at effective levels in the NOSDS wherein they may be present in an amount between about 5-50% of the total amount:
  aspartic acid
  $C_1$-$C_6$ partial or di-ester of aspartic acid
  glutamic acid
  $C_1$-$C_6$ partial or di-ester of glutamic acid
  maleic anhydride
  itaconic anhydride
  citraconic anhydride
  citric acid
  $C_1$-$C_6$ partial or tri-ester of citric acid
  acrylic acid
  $C_1$-$C_6$ partial or full ester of acrylic acid
  methacrylic acid
  $C_1$-$C_6$ partial or full ester of methacrylic acid
  maleic acid
  $C_1$-$C_6$ partial or di-ester of maleic acid
  itaconic acid
  $C_1$-$C_6$ partial or di-ester of itaconic acid
  citraconic acid
  $C_1$-$C_6$ partial or di-ester of citraconic acid In a variation, the fertilizer additive may further comprise one or more pesticides, herbicides, fungicides and/or insecticide.

In a variation, the fertilizer additive may further comprising one or more nitrification inhibitors wherein the one or more nitrification inhibitors is selected from the group consisting of 2-chloro-6-trichloromethyl)pyridine, 4-amino-1,2,4-6-triazole-HCl, 2,4-diamino-6-trichloromethyltriazine CL-1580, dicyandiamide, thiourea, 1-mercapto-1,2,4-triazole, 3,4-dimethylpyrazole phosphate, and 2-amino-4-chloro-6-methylpyrimidine.

In an embodiment, the fertilizer additive may further comprise one or more urease inhibitors wherein the one or more urease inhibitors is selected from the group consisting of phosphoric triamides, thiophosphoric triamides and alkylated thiophosphoric triamides, wherein the alkylated thiophosphoric triamides has one or more alkyl groups that independently contain between 1 and 6 carbon atoms.

In a variation, the fertilizer and/or seed additive may comprise one or more nitrification inhibitors wherein the one or more nitrification inhibitors comprise dicyandiamide, the one or more [P(OA)]s comprise polyaspartic acid and the one or more urease inhibitors comprise phosphoric triamides. Alternatively, the one or more urease inhibitors may comprise a phosphoramide.

In an embodiment, the present invention relates to a method of making a composition to be added as a coating to the surface of a fertilizer granules and/or seeds comprising:

heating a mixture comprises one or more [P(OA)]s and/or their salts in a NOSDS comprised of a) one or more protic solvents from the group consisting of 1) an alcohol from the family of $C_{1-10}$ alkanols, 2) polyols selected from the group consisting of trimethylol propane, trimethylol ethane, pentaerythritol, sorbitol and sorbitan, glucose, fructose, galactose, and/or glycerin, 3) poly($C_{1-10}$ alkylene) glycols, 4) alkylene glycols selected from the group consisting of ethylene, 1,3 propylene glycol, 1,2 propylene glycol, and/or butylene glycol, 5) isopropylidene glycerol 6) alkylene glycol alkyl ethers selected from the group consisting of tripropylene glycol methyl ether, tripropylene glycol butyl ether, dipropylene glycol butyl ether and/or dipropylene glycol butyl ether, 7) ethyl, propyl, or butyl lactate, 8) an alkanolamine selected from the group consisting of ethanolamine, diethanolamine, dipropanolamine, methyl diethanolamine, monoisopropanolamine and/or triethanolamine and/or 9) glycerol carbonate.

b) and/or one or more aprotic solvents from the group consisting of 1) Dimethyl Sulfoxide and/or 2) dialkyl, diaryl, or alkylaryl sulfoxide(s) having the formula:

$$R_1S(O)_xR_2$$

wherein $R_1$ and $R_2$ are each independently a $C_{1-6}$ alkylene group, an aryl group, or $C_{1-6}$ alkylenearyl group or $R_1$ and $R_2$ with the sulfur to which they are attached form a 4 to 8 membered ring wherein $R_1$ and $R_2$ together are a $C_{1-6}$ alkylene group which optionally contains one or more atoms selected from the group consisting of O, S, Se, Te, N, and P in the ring and x is 1 or 2.

3) alkylene carbonates selected from the group consisting of ethylene carbonate, propylene carbonate and/or butylene carbonate, 4) polyols capped with acetate or formate wherein the polyol portion may be one or more of ethylene glycol, 1,3 propylene glycol, 1,2 propylene glycol, butylene glycol, trimethylol propane, trimethylol ethane, pentaerythritol, sorbitol and sorbitan, glucose, fructose, galactose and/or glycerin, 5) alkylene glycol alkyl ethers acetates selected from the group consisting of dipropylene glycol methyl ether acetate, tripropylene glycol methyl ether acetate, and/or tripropylene glycol butyl ether acetate and/or, 6) isophorone, 7) dimethylsuccinate, dimethyl adipate, diethyl glutarate, and/or dimethyl glutarate, 8) dimethylacetamide, dimethylformamide, dimethyl-2-imidazolidinone 9) hexamethylphosphoramide, 10) 1,2-dimethyloxethane, 2-methoxyethyl ether, 11) cyclohexylpyrrolidone and/or 12) limonene;

and cooling the mixture to a temperature that optionally allows addition of one or more of surfactants, buffers, fragrance/odor masking agents, colorants, micro-nutrients, dispersed urease inhibitor(s), dispersed nitrification inhibitor(s), pesticide(s), herbicide(s) fungicide(s) and/or flow modifiers.

In an embodiment, the method may further comprise adding the composition to a fertilizer and/or seed.

In a variation, the fertilizer and/or seed additive may contain one or more [P(OA)]s and/or their salts comprised of the following monomers as homopolymers, copolymers and/or terpolymers at effective levels in the NOSDS wherein they may be present in an amount between about 5-50% of the total:

aspartic acid
$C_1$-$C_6$ partial or di-ester of aspartic acid
glutamic acid
$C_1$-$C_6$ partial or di-ester of glutamic acid
maleic anhydride
itaconic anhydride
citraconic anhydride
citric acid
$C_1$-$C_6$ partial or tri-ester of citric acid
acrylic acid
$C_1$-$C_6$ partial or full ester of acrylic acid
methacrylic acid
$C_1$-$C_6$ partial or full ester of methacrylic acid
maleic acid
$C_1$-$C_6$ partial or di-ester of maleic acid
itaconic acid
$C_1$-$C_6$ partial or di-ester of itaconic acid
citraconic acid and/or
$C_1$-$C_6$ partial or di-ester of citraconic acid wherein the one or more [P(OA)]s are present at a level that is between about 5-50% of a total composition.

In a variation, the method may use dispersed nitrification inhibitors that is/are one or more members selected from the group consisting of 2-chloro-6-trichloromethylpyridine, 4-amino-1,2,4-6-triazole-HCl, 2,4-diamino-6-trichloromethyltriazine CL-1580, dicyandiamide, thiourea, 1-mercapto-1,2,4-triazole, 2-amino-4-chloro-6-methylpyrimidine, and 3,4-dimethylpyrazole phosphate.

In an embodiment, the method may comprise one or more dispersed urease inhibitors wherein they are one or more members selected from the group consisting of phosphoric triamides, thiophosphoric triamides and alkylated thiophosphoric triamides, wherein the alkylated thiophosphoric triamides has one or more alkyl groups that independently contain between 1 and 6 carbon atoms.

In a variation, the method may comprise a dispersed nitrification inhibitor and a dispersed urease inhibitor wherein the dispersed nitrification inhibitor comprises dicyandiamide and the dispersed urease inhibitor comprises phosphoric triamides. Alternatively, the dispersed urease inhibitor may comprise a phosphoramide.

In a variation, the method may use a composition that is substantially free of water. Substantially free of water means less than about 1% water.

In a variation, the present invention relates to a composition comprising one or more Poly (organic acids), [P(OA)] s, and/or their salt(s) and one or more of a Non-aqueous Organo Solvent Delivery System (NOSDS), wherein said composition is a stable dispersion ideally suited to coat man-made and/or natural fertilizer components and/or seeds wherein the [P(OA)]s are homopolymers, copolymers and/or terpolymers that are comprised of one or more of the following monomers:

aspartic acid, glutamic acid, maleic acid, itaconic acid, citraconic acid, citric acid, acrylic acid, methacrylic acid, itaconic acid, and citraconic acid, their $C_{1-6}$ esters, anhydrides, and imides, or their salts;

and wherein the NOSDS is comprised of one or more of;
a) protic solvents selected from the group consisting of:
a C1-10 alcohol, 2) one or more polyols selected from the group consisting of trimethylol propane, trimethylol ethane, pentaerythritol, sorbitol and sorbitan, glucose, fructose, galactose, and glycerin, 3) poly(C1-10 alkylene) glycols, 4)

alkylene glycols selected from the group consisting of ethylene glycol, 1,3 propylene glycol, 1,2 propylene glycol, and butylene glycol 5) isopropylidene glycerol 6) alkylene glycol alkyl ethers selected from the group consisting of tripropylene glycol methyl ether, tripropylene glycol butyl ether, dipropylene glycol butyl ether and dipropylene glycol butyl ether, 7) ethyl, propyl, or butyl lactate, 8) an alkanolamine selected from the group consisting of ethanolamine, diethanolamine, dipropanolamine, methyl diethanolamine, monoisopropanolamine and triethanolamine and 9) glycerol carbonate and/or b) one or more aprotic solvents comprising one or more of 1) dimethyl sulfoxide 2) a dialkyl sulfoxide, diaryl sulfoxide, or an alkylaryl sulfoxide having the formula:

$R_1S(O)_xR_2$ wherein $R_1$ and $R_2$ are each independently a $C_{1-6}$ alkyl group, an aryl group, or $C_{1-3}$ alkylenearyl group, or $R_1$ and $R_2$ with the sulfur to which they are attached form a 4 to 7 membered ring wherein $R_1$ and $R_2$ together are a $C_{1-6}$ alkylene group which optionally contains one or more atoms selected from the group consisting of O, S, Se, Te, N, and P in the ring and x is 1 or 2 or 3) an alkylene carbonate selected from the group consisting of ethylene carbonate, propylene carbonate and butylene carbonate, 4) a polyol capped with acetate or formate wherein the polyol portion is one or more of ethylene glycol, 1,3 propylene glycol, 1,2 propylene glycol, butylene glycol, trimethylol propane, trimethylol ethane, pentaerythritol, sorbitol, sorbitan, glucose, fructose, galactose or glycerin, 5) an alkylene glycol alkyl ether acetates selected from the group consisting of dipropylene glycol methyl ether acetate, tripropylene glycol methyl ether acetate, and tripropylene glycol butyl ether acetate, 6) isophorone, 7) dimethylsuccinate, dimethyl adipate, diethyl glutarate, and/or dimethyl glutarate, 8) dimethylacetamide, dimethylformamide, dimethyl-2-imidazolidinone 9) hexamethylphosphoramide, 10) 1,2-dimethyloxyethane, 2-methoxyethyl ether, 11) cyclohexylpyrrolidone and/or 12) limonene.

In an embodiment, the salts are derived from metals, metal hydroxides, metal alkylates, metal carbonates, ammonia, ammonium hydroxide, or organoamines.

In an embodiment, wherein the metals in the metals, metal hydroxides, metal alkylates, or metal carbonates comprise one or more of Na, K, Mg, Ca, Fe, Zn, Mn, Cu, Co, Mo or Ni.

In a variation, the organoamines comprise one or more of mono $C_{1-6}$ amine, di $C_{1-6}$ amine, tri $C_{1-6}$ amine, mono ethanol amine, diethanol amine, triethanol amine, monoisopropanol amine, diisopropanol amine, triisopropanol amine, ethylene diamine diethylene triamine, triethylene tetraamine, or tetraethylene pentamine.

In a variation, the composition comprises one or more protic solvents or one or more aprotic solvents.

In an embodiment, the composition:
 i Is Environmentally safe;
 ii Has flashpoints above 145° F.;
 iii Is inherently rated safe for contact with humans and animals;
 iv Provides stable dispersions of [P(OA)]s or their salts at levels of 1-50% in the NOSDS at storage temperatures down to at least 10° C.;
 v Provides improved, even application of a coating to fertilizer granules and seeds while not causing clumping of the fertilizer granules, premature seed germination and does not support the growth of mold and mildew on seeds; and
 vi Will not detrimentally impact the stability of alkyl thiophosphoric triamides.

In a variation, the NOSDS comprises one or more protic solvents wherein the [P(OA)]s to the one or more protic solvent ratio is between about 90/10 to 10/90.

In a variation, the one or more [P(OA)]s comprises a potassium salt of a polyaspartate wherein the potassium salt of the polyaspartate is present in an amount that is between about 10-45% of a total composition amount and the NOSDS of the formulation is ethylene glycol.

In an embodiment, the composition may further comprise one or more of surfactants, buffers, fragrance/odor masking agents, colorants, micro-nutrients, dispersed urease inhibitor(s), dispersed nitrification inhibitor(s), pesticide(s), fungicides(s), herbicide(s), insecticide(s) or flow modifiers.

In an embodiment, the composition is substantially free of water.

In an embodiment, the present invention relates to a process for producing the composition, wherein said process comprises procuring one or more of the following monomers:

aspartic acid, glutamic acid, maleic acid, itaconic acid, citraconic acid, citric acid, acrylic acid, methacrylic acid, itaconic acid, and citraconic acid, their $C_{1-6}$esters, anhydrides, and imides, or their salts; and dispersing said one or more monomers into an aprotic solvent to create a dispersion wherein said aprotic solvent comprises one or more of 1) dimethyl sulfoxide 2) dialkyl, diaryl, or alkylaryl sulfoxide(s) having the formula:

$R_1S(O)_xR_2$ wherein $R_1$ and $R_2$ are each independently a $C_{1-6}$ alkylene group, an aryl group, or $C_{1-3}$alkylenearyl group or $R_1$ and $R_2$ with the sulfur to which they are attached form a 4 to 8 membered ring wherein $R_1$ and $R_2$ together are a $C_{1-6}$ alkylene group which optionally contains one or more atoms selected from the group consisting of O, S, Se, Te, N, and P in the ring and x is 1 or 2 or 3) an alkylene carbonate selected from the group consisting of ethylene carbonate, propylene carbonate and butylene carbonate, 4) a polyol capped with acetate or formate wherein the polyol portion is one or more of ethylene glycol, 1,3 propylene glycol, 1,2 propylene glycol, butylene glycol, trimethylol propane, trimethylol ethane, pentaerythritol, sorbitol, sorbitan, glucose, fructose, galactose and/or glycerin, 5) an alkylene glycol alkyl ether acetate selected from the group consisting of dipropylene glycol methyl ether acetate, tripropylene glycol methyl ether acetate, and tripropylene glycol butyl ether acetate, 6) isophorone, 7) dimethylsuccinate, dimethyl adipate, diethyl glutarate, and/or dimethyl glutarate, 8) dimethylacetamide, dimethylformamide, dimethyl-2-imidazolidinone 9) hexamethylphosphoramide, 10) 1,2-dimethyloxethane, 2-methoxyethyl ether, 11) cyclohexylpyrrolidone and/or 12) limonene; heating said dispersion to a polymerization temperature with or without a catalyst, held at polymerization temperature until a molecular weight 1500 to 10000 grams/mol is achieved.

In an embodiment, the process may further comprising neutralizing the one or more monomers with one or more metals, wherein said one or more metals comprise elemental metals, metal oxides, metal hydroxides, metal alkylates or metal carbonates, or with one or more nitrogen containing compounds comprising ammonia, ammonium hydroxide, or organoamines.

In an embodiment of the process, the one or more metals in the elemental metals, metal oxides, metal hydroxides, metal alkylates or metal carbonates comprise Na, K, Mg, Ca, Fe, Zn, Mn, Cu, Co, Mo or Ni.

In a variation, the organoamines comprise one or more of mono $C_{1-6}$ amine, di $C_{1-6}$ amine, tri $C_{1-6}$ amine, mono ethanol amine, diethanol amine, triethanol amine, monoisopropanol amine, diisopropanol amine, triisopropanol amine, ethylene diamine diethylene triamine, triethylene tetraamine, or tetraethylene pentamine. In an embodiment, the present invention relates to a process for producing the composition, wherein said process comprises procuring one or more of the following monomers:

aspartic acid, glutamic acid, maleic acid, itaconic acid, citraconic acid, citric acid, acrylic acid, methacrylic acid, itaconic acid, and citraconic acid, their anhydrides, and imides, or their salts;

wherein said one or more monomers is/are dispersed into one or more protic solvents where the molar ratio of protic solvent to monomer(s) may be any ratio between about 0.5 to 1 and 10 to 1 and/or the weight ratio of the NOSDS to reactive monomer is 10% to 90% and 90% to 10% which is heated to 120-190° C. to form an ester wherein the one or more protic solvents are selected from the group consisting of:

1) an alcohol from the family of $C_{1-10}$ alkanols, 2) polyols selected from the group consisting of trimethylol propane, trimethylol ethane, pentaerythritol, sorbitol, sorbitan, glucose, fructose, galactose, and glycerin, 3) poly($C_{1-10}$ alkylene) glycols, 4) alkylene glycols selected from the group consisting of ethylene glycol, 1,3 propylene glycol, 1,2 propylene glycol, and butylene glycol, 5) isopropylidene glycerol 6) alkylene glycol alkyl ethers selected from the group consisting of tripropylene glycol methyl ether, tripropylene glycol butyl ether, dipropylene glycol butyl ether and dipropylene glycol butyl ether, 7) ethyl, propyl, or butyl lactate, 8) an alkanolamine selected from the group consisting of ethanolamine, diethanolamine, dipropanolamine, methyl diethanolamine, monoisopropanolamine and triethanolamine and 9) glycerol carbonate;

and heating said dispersion to a polymerization temperature with or without catalyst, until a molecular weight of 1500 to 10000 g/mol is achieved;

and to which one or more aprotic solvents is optionally added wherein said one or more aprotic solvents comprise 1) dimethyl sulfoxide 2) dialkyl, diaryl, or alkylaryl sulfoxide(s) having the formula:

$R_1S(O)_xR_2$ wherein $R_1$ and $R_2$ are each independently a $C_{1-6}$ alkylene group, an aryl group, or $C_{1-3}$ alkylenearyl group or $R_1$ and $R_2$ with the sulfur to which they are attached form a 4 to 7 membered ring wherein $R_1$ and $R_2$ together are a $C_{1-6}$ alkylene group which optionally contains one or more atoms selected from the group consisting of O, S, Se, Te, N, and P in the ring and x is 1 or 2;

3) alkylene carbonates selected from the group consisting of ethylene carbonate, propylene carbonate and butylene carbonate, 4) polyols capped with acetate or formate wherein the polyol is one or more of ethylene glycol, 1,3 propylene glycol, 1,2 propylene glycol, butylene glycol, trimethylol propane, trimethylol ethane, pentaerythritol, sorbitol, sorbitan, glucose, fructose, galactose and/or glycerin, 5) alkylene glycol alkyl ethers acetates selected from the group consisting of dipropylene glycol methyl ether acetate, tripropylene glycol methyl ether acetate, and tripropylene glycol butyl ether acetate, 6) isophorone, 7) dimethylsuccinate, dimethyl adipate, diethyl glutarate, and/or dimethyl glutarate, 8) dimethylacetamide, dimethylformamide, dimethyl-2-imidazolidinone 9) hexamethylphosphoramide, 10) 1,2-dimethyloxethane, 2-methoxyethyl ether, 11) cyclohexylpyrrolidone and/or 12) limonene.

In a variation of the process, the ester may be further saponified generating a carboxylic acid salt wherein said salt is derived from metals, metal hydroxides, metal alkylates, metal carbonates, ammonia, ammonium hydroxide, or organoamines.

In a variation, the metal in the metals, metal hydroxides, metal alkylates, or metal carbonates is Na, K, Mg, Ca, Fe. Zn, Mn, Cu, Co, Mo and/or Ni.

In a variation, the organoamines comprise one or more of mono $C_{1-6}$ amine, di $C_{1-6}$ amine, tri $C_{1-6}$ amine, mono ethanol amine, diethanol amine, triethanol amine, monoisopropanol amine, diisopropanol amine, triisopropanol amine, ethylene diamine diethylene triamine, triethylene tetraamine, or tetraethylene pentamine.

In a variation, the present invention relates to a process for producing the composition, wherein said process comprises procuring a polymer that comprises polysuccinimide, polyaspartic acid, polyglutamic acid, and/or a copolymer of aspartic acid and glutamic acid and/or salts thereof;

wherein said polymer is dispersed within a NOSDS at a % weight ratio of 10:90% to 90:10% of polymer: NOSDS, wherein the NOSDS comprises a) of one or more protic solvents which are heated to 120-190° C. to form an ester and wherein the one or more protic solvents are selected from the group consisting of:

1) an alcohol from the family of $C_{1-10}$ alkanols, 2) polyols selected from the group consisting of trimethylol propane, trimethylol ethane, pentaerythritol, sorbitol, sorbitan, glucose, fructose, galactose, and glycerin, 3) poly($C_{1-10}$ alkylene) glycols, 4) alkylene glycols selected from the group consisting of ethylene glycol, 1,3 propylene glycol, 1,2 propylene glycol, and butylene glycol, 5) isopropylidene glycerol 6) alkylene glycol alkyl ethers selected from the group consisting of tripropylene glycol methyl ether, tripropylene glycol butyl ether, dipropylene glycol butyl ether and dipropylene glycol butyl ether, 7) ethyl, propyl, or butyl lactate, 8) an alkanolamine selected from the group consisting of ethanolamine, diethanolamine, dipropanolamine, methyl diethanolamine, monoisopropanolamine and triethanolamine and 9) glycerol carbonate.

In a variation, the ester may be saponified.

In an embodiment, the salts may be derived from metals, metal hydroxides, metal alkylates, metal carbonates, ammonia, ammonium hydroxide, or organoamines and the metal in the metals, metal hydroxides, metal alkylates, or metal carbonates are one or more of Na, K, Mg, Ca, Fe, Zn, Mn, Cu, Co, Mo or Ni.

In a variation, the organoamines comprise one or more of mono $C_{1-6}$ amine, di $C_{1-6}$ amine, tri $C_{1-6}$ amine, mono ethanol amine, diethanol amine, triethanol amine, monoisopropanol amine, diisopropanol amine, triisopropanol amine, ethylene diamine diethylene triamine, triethylene tetraamine, or tetraethylene pentamine.

The following EXAMPLEs are presented to illustrate certain embodiments of the present invention:

EXAMPLE 1

400 grams of ethylene glycol was charged to a vessel, placed under strong agitation and then heated to 60° C. 222.2 grams of polyaspartate-potassium salt/90% NVS was then slowly charged to the vessel and mixed until completely dissolved. Once dissolved, the mixture was placed under high shear agitation by using an overhead mixer equipped with a cowles blade while maintaining the batch temperature at 60-80° C. for 1 hour. After one hour the vessel was sealed and a vacuum of 200 mm or less was pulled to remove water. The mixture was cooled to <30° C. and then packaged off in an appropriate container.

EXAMPLE 2

120 grams of Example 1 was heated to 60° C., placed under agitation and then 80 grams of propylene glycol was charged to the vessel. The combination was mixed for 30 minutes and then cooled to <40° C. and packaged off.

EXAMPLE 3

120 grams of Example 1 was heated to 60° C., placed under agitation and then 80 grams of glycerin were charged to the vessel. The combination was mixed for 30 minutes and then cooled to <40° C. and packaged off.

EXAMPLE 4

120 grams of Example 1 was heated to 60° C., placed under agitation and then 40 grams of ethylene glycol and 40 grams of tripropylene glycol monomethyl ether were charged to the vessel. The combination was mixed for 30 minutes and then cooled to <40° C. and packaged off.

EXAMPLE 5

450 grams of ethylene glycol was charged to a vessel, placed under strong agitation and then heated to 60° C. 300 grams of a polysuccinimide (5000 average molecular weight) was then slowly charged to the vessel and mixed until completely dispersed. The mixture was then heated to 140° C. and held until all particles dissolved (~1.5 hrs). The mix was then cooled to 50° C. 147 grams of KOH flakes were slowly charged to the mix at a rate to maintain temperature of 60-80> C. The formulation was mixed until all KOH flakes (100%) were dissolved. The mix was then cooled to 40° C. and then placed under high shear agitation by using an overhead mixer equipped with a cowles blade while maintaining the batch temperature at 60-80° C., for 1 hour. After one hour, an FTIR scan was run to determine if the presence of ester had been eliminated. The mixture was sampled every 30 minutes until traces of esters had been eliminated. The mixture was cooled to <30° C. and then packaged off in an appropriate container.

EXAMPLE 6

58.54 grams of Example 5 was charged to a vessel and then placed under strong agitation and then heated to 60° C. 65.4 grams of ethylene glycol were then charged to the vessel and mixed for 30 minutes. After 30 minutes, the mixture was cooled to 38° C. and then packaged off in an appropriate container.

EXAMPLE 7

58.54 grams of Example 5 was charged to a vessel and then placed under strong agitation and then heated to 60° C. 35.4 grams of ethylene glycol and 30 grams of dimethyl glutarate were then charged to the vessel and mixed for 30 minutes. After 30 minutes, the mixture was cooled to 38° C. and then packaged off in an appropriate container.

EXAMPLE 8

58.54 grams of Example 5 was charged to a vessel and then placed under strong agitation and then heated to 60° C. 65.4 grams of glycerin were then charged to the vessel and mixed for 30 minutes. After 30 minutes, the mixture was cooled to 38° C. and then packaged off in an appropriate container.

EXAMPLE 9

104.3 grams of Example 5 was charged to a vessel and then placed under strong agitation and then heated to 60° C. 45.7 grams of ethylene glycol were then charged to the vessel and mixed for 30 minutes. After 30 minutes, the mixture was cooled to 38° C. and then packaged off in an appropriate container.

EXAMPLE 10

183.12 grams of dimethyl sulfoxide was charged to a vessel, placed under strong agitation and then heated to 60° C. 78.48 grams of a polysuccinimide (5000 average molecular weight) was then slowly charged to the vessel and mixed until completely dispersed. 72.74 grams of DI water was charged to the vessel and then 49.07 grams of NH4OH/28% were slowly charged holding the mixture's temperature at 60-80° C. It was mixed for one hour and then placed under a vacuum of 50 mm with a slight $N_2$ sparge until distillation ceases. The mix was then cooled to 40° C. and then packaged off in an appropriate container.

EXAMPLE 11

282.52 grams of dimethyl sulfoxide was charged to a vessel, placed under strong agitation and then heated to 60° C. 146.23 grams of a partial sodium hydroxide neutralized polyacrylic acid (Kemira 5847) was then charged to the vessel and mixed for 15 minutes. A vacuum of 38 mm was applied until distillation ceases. The mix was then cooled to 40° C. and then packaged off in an appropriate container.

EXAMPLE 12

150 grams of ethylene glycol, 150 grams of L-aspartic acid and 1.5 grams of phosphoric acid/85% were charged to a vessel, then placed under strong agitation and then heated to 185° C. After 5 hrs, 64.3 grams of distillate were collected and the batch was cooled to 60° C. 97.44 grams KOH flake (100%) was then slowly charged to the vessel at a rate that allowed the batch temperature to be 60-80° C. and mixed until completely dissolved. It was then placed under high shear agitation by using an overhead mixer equipped with a cowles blade while maintaining the batch temperature at 60-80° C. for 1 hour. After one hour, an FTIR scan was run to determine if the presence of ester had been eliminated. The mixture was sampled every 30 minutes until traces of esters had been eliminated. After the ester peak was eliminated, 281.08 grams of ethylene glycol were charged and the resulting mixture was mixed for 30 minutes. The mix was then cooled to 40° C. and then packaged off in an appropriate container.

EXAMPLE 13

71.58 grams of acetone was charged to a vessel and then 12.48 grams of maleic anhydride and 16.49 grams itaconic anhydride and 0.98 grams of benzoyl peroxide were charged to the vessel. Very slow agitation was used until the maleic briquettes were dissolved. The vessel was then sealed and inerted with $N_2$ and the batch was heated to 60° C. and held at 55-65° C. for five hours. After five hours, the batch was cooled to 35° C. and 43.45 grams of ethylene glycol was charged. A vacuum was then pulled on the vessel slowly decreasing the pressure based on the distillation rate while heating the batch back to 55-65° C. When distillation ceases, the vacuum was broken with $N_2$ and then 15.39 grams of KOH flake (100%) were slowly charged in order to hold temperature at 60-80° C. When KOH flakes were completely dissolved, the mix was placed under high shear agitation by using an overhead mixer equipped with a cowles blade while maintaining the batch temperature at 60-80° C. for 1 hour. Thereafter the mix was checked using an FTIR scan. The FTIR scan was run and checked every 30 minutes for the disappearance of the ester peak. After the ester peak disappeared, 89.63 grams of ethylene glycol were charged, and the batch was then mixed 30 minutes and cooled to <40° C. and then off-loaded into the appropriate container.

EXAMPLE 14

45 grams of Example 12 were mixed with 10 grams of N-Yield (a urease inhibitor in a non-aqueous liquid), 40 grams of N-Bound (a nitrification inhibitor in a non-aqueous liquid) and 5 grams of glycerin. The resulting fluid product was then off-loaded into the appropriate container.

EXAMPLE 15

99.5 grams of DMSO, 99.5 grams of l-aspartic acid and 1.0 grams of phosphoric acid/85% were charged to a vessel, then placed under strong agitation and then heated to 155° C. After 4.5 hrs. 28.49 grams of distillate were collected and the batch was cooled to 80° C. 85.09 grams $NH_4OH$ (28%) was then slowly charged to the vessel at a rate that allowed the batch temperature to be 60-80° C. over a 5 hour period. The reactor was sealed and heated to 95 C and held for 17 hrs and then checked by IR to insure the ester was eliminated. 352.88 gms of DMSO were charged and then heated back to 80 C, 68.07 gms of DCD were charge and mixed until particles dissolved. The batch was cooled to 35 C and then 17.02 NBPT were charged and mixed until particles dissolved. 51.05 gms of propylene glycol were charged and mix 15 minutes. The mixture was then package and 50 gins placed in a 50 C oven for 3 days. After 3 days at 50 C, the product showed no signs of instability.

EXAMPLE 16

43.57 grams of polysuccinimide (molecular weight 3000-5000), 119.12 grams of ethylene glycol were charged to a reactor, placed under agitation and heated to 140° C. until all particles were solubilized. 2.41 grams of zinc oxide were charged while holding temperature at 120° C. until appearance of mixture transitioned from milky to translucent. The reactor was then cooled to 40 C and 19.19 of KOH/45% were slowed charged while holding the temperature less than 80° C. The product was then cooled to <40° C. and packaged off.

EXAMPLE 17

250 grams of ethylene glycol, 250 grams of L-aspartic acid and 2.94 grams of phosphoric acid/85% were charged to a vessel, then placed under strong agitation and then heated to 150° C. After 5 hours no particles were observed and 67.6 grams of distillate were collected. The batch was cooled to 120° C. and 23.67 grams of magnesium oxide was slowly charged and dispersed with 15 minutes if agitation. 10.57 grams of distilled water was then charged to the vessel and the contents were agitated until contents cleared in approximately 5.5 hours. The contents of the vessel were then cooled to 60° C., 103.21 grams KOH flake (100%) was then slowly charged to the vessel at a rate that allowed the batch temperature to be maintained at 60-80° C. and mixed until completely dissolved. It was then mixed an additional hour. After one hour, an FTIR scan was run to determine if the presence of ester had been eliminated. The mixture was sampled every 30 minutes until traces of esters had been eliminated. After the ester peak was eliminated, the batch was cooled to 40° C. and then placed under high shear agitation by using rotor stator mixer while maintaining the batch temperature at less than 80° C. by using an ice bath and by slowly increasing the RPM's of the mixer to 10,000 over a 1 hour time period. After the high shear mixing, 233.66 grams of ethylene glycol were charged and the resulting mixture was mixed for 30 minutes. The mix was cooled to <40° C. and then packaged off in an appropriate container.

EXAMPLE 18

128.46 grams of ethylene glycol, 62.06 grams of L-aspartic acid and 0.99 grams of phosphoric acid/85% were charged to a vessel, then placed under strong agitation and heated to 150° C. After 5 hours no particles were observed and 16.22 grams of distillate were collected. The batch was cooled to 120° C. and 7.67 grams of zinc oxide was slowly charged and dispersed with 15 minutes if agitation. 1.70 grams of distilled water was then charged to the vessel and the contents were agitated until the contents cleared in approximately 8.5 hours. The contents of the vessel were then cooled to 60° C., 14.27 grams KOH flake (100%) was then slowly charged to the vessel at a rate that allowed the batch temperature to be maintained at 60-80° C. and mixed until completely dissolved. It was then mixed an additional hour. After one hour, an FTIR scan was run to determine if the presence of ester had been eliminated. The mixture was sampled every 30 minutes until traces of esters had been eliminated. After the ester peak was eliminated, the batch was then cooled to <40° C. and then packaged off in an appropriate container.

EXAMPLE 19

333.9 grams of DMSO were charged to a reactor, placed under agitation and then 477 grams of sorbitol/70% were charged to the reactor. The mixture was then heated to 75°

C. and placed under 20 mm of vacuum to strip out residual water. Once the formation of distillate ceased, the mixture was cooled to 40° C. and 611.59 grams of DMSO/sorbitol were recovered. In a mixing vessel, 71.3 grams of Example #5 were charged followed by 31.1 grams of the DMSO/sorbitol mixture and 31.1 grams of DMSO. The combination was mixed for 15 minutes and then 16.5 grams of KOH flakes were slowly charged holding the temperature below 80° C. The product was cooled below 40° C. and packaged.

EXAMPLE 20

In a reactor, 122.24 grams of L-aspartic acid and 76.77 grams of propylene glycol were charged, placed under agitation and heated to 170° C. It was held at 17° C. until all particles disappeared. 199.04 grams of PG and 14.92 grams of zinc oxide were charged to the reactor while maintaining the batch temperature at 120-160° C. After batch appearance transitioned from milky to translucent, the batch was cooled to 40° C. and 61.81 grams of KOH/45% were slowly charged to reactor while maintaining the batch temperature below 80° C. The product was mixed 14 hours at 80° C. to saponify all ester linkages. The batch was then cooled to less than 40° C. and packaged

EXAMPLE 21

In a reactor, charge 450.77 grams glycerin and 300 grams polysuccinimide (3000-5000 molecular weight) and heat to 140° C. and hold until all particles have reacted/dissolved. Cool to 40° C.

EXAMPLE 22

In a mixing vessel under agitation, 48.8 grams of Example 21 and 28.6 grams of glycerin were charged. Then 22.6 grams of KOH/45% were slowly charged holding temp less than 80° C. during charge. After charging KOH, hold at 80° C. until ester linkages have been saponified. Cool to less than 40° C. and package off.

EXAMPLE 23

In a mixing vessel under agitation, charge 48.8 grams of Example 22 and 28.6 grams of propylene glycol. Slowly charge 22.6 grams of KOH/45% holding temp less than 80° C. during charge. After charging KOH, hold at 80° C. until ester linkages have been saponified. Cool to less than 40° C. and package off.

EXAMPLE 24

60.55 grams of ethylene glycol, 130.01 grams of L-aspartic acid (ethylene glycol/aspartic acid molar ratio of 1:1 and a weight ratio of 32% to 68%) and 0.95 grams of phosphoric acid/85% were charged to a vessel, then placed under very low agitation and then slowly heated to 170° C. over a period of five hours. The rate of temperature rise was dependent on ability to increase agitation speed as high as product solids and viscosity would allow so as to not allow the product to burn. After 5 hours no particles were observed and 37.33 grams of distillate were collected. 279.42 grams of ethylene glycol were charged and the batch was cooled to 60° C. 49.82 grams KOH flake (100%) was then slowly charged to the vessel at a rate that allowed the batch temperature to be maintained at 60-80° C. and mixed until completely dissolved. It was then mixed and heated to 80 C and held an additional hour. The mix was cooled to <40° C. and then packaged off in an appropriate container.

EXAMPLE 25

48.4 grams of ethylene glycol were charge to a reactor, placed under agitation and a nitrogen sparge and heated to 90° C. 113.7 grams of a polysuccinimide (molecular weight 3000-5000) were slowly added to the reactor while increasing the agitation as needed and holding the temperature between 80 and 100° C. The very viscous product was then heated to 120° C. and 37.9 grams of addition polysuccinimide (molecular weight 3000-5000) were slowly charged to the reactor raising the molar ratio of PSI to Ethylene Glycol to 1:0.5 and the weight ratio 75.8% to 24.2%. The agitation was increased as product viscosity allowed. After 30 minutes the batch temperature was increased to 150° C. After 60 minutes at 150° C., all particles were dissolved. 384.48 grams of ethylene glycol were charged and the batch was cooled to 60 C. 63.46 grams of KOH (100%) were slowly charged to the reactor while maintaining the batch temperature 60-80° C. utilizing a cooling bath to assist in removing the heat from the exothermic neutralization. After all the KOH had been charged and was dissolved, the batch temperature was held at 80° C. under strong agitation for 3 hours. The batch was then cooled to <40 C and packaged off in an appropriate container.

EXAMPLE 26

A dye was required in order to determine effectiveness of coating grams of each Example was placed under agitation and 0.4 grams of a 20% FD&C Blue #1 in a solvent was added to the 20 grams of each example. Each example was mixed for 15 minutes after addition of dye. Included in the testing were two aqueous commercial products, Avail & P-Max Sample ID Prepared for Coating Test

| Example ID | Sample ID |
|---|---|
| Example 2 | Sample 1 |
| Example 3 | Sample 2 |
| Example 4 | Sample 3 |
| Example 6 | Sample 4 |
| Example 7 | Sample 5 |
| Example 8 | Sample 6 |
| Example 9 | Sample 7 |
| Example 10 | Sample 8 |
| Example 11 | Sample 9 |
| Example 12 | Sample 10 |
| Example 13 | Sample 11 |
| Example 14 | Sample 12 |
| Example 15 | Sample 13 |
| Example 16 | Sample 14 |
| Example 17 | Sample 15 |
| Example 18 | Sample 16 |
| Example 19 | Sample 17 |
| Example 20 | Sample 18 |
| Avail | Sample 19 |
| P-Max | Sample 20 |
| Example 23 | Sample 21 |
| Example 24 | Sample 22 |
| Example 25 | Sample 23 |

EXAMPLE 27

200 grams of a technical grade of DAP was charged to a glass 1000 ml beaker. The beaker was then placed under an overhead agitator with an anchor agitator blade. The height of the beaker was adjusted such that the bottom of the anchor agitator blade was close to the bottom of the glass beaker. The RPM of the overhead stirrer was adjusted to 200 RPM's and the DAP was agitated for 30 seconds. After 30 seconds, a 2.0 gram of a sample of Example 21 was charged within 10 seconds. A stopwatch was used for timing to complete coating. (Visually: when 95% of DAP particles were colored blue). This was repeated for each of the tested samples from Example 26.

After coating, the 200 grams of coated DAP was poured in a one quart jar and 200 grams of weight were placed on top of each sample in the quart jar. After setting for 48 hours, the weight was removed and a lid was placed on each quart jar. Each jar was then inverted and rated for flowability. If the contents of a jar did not flow in 5 minutes, a wooden handle of a 4 inch spatula was used to tap the jar to encourage flow. Flow rating is as follows:

| Rating | Action after inversion |
| --- | --- |
| 1 | Instant flow |
| 2 | >70% flow in 1 minute |
| 3 | >70% flow in 1-3 minutes |
| 4 | >70% flow in 3-5 minutes |
| 5 | >70% flow after 1-2 taps |
| 6 | >70% flow after 3-4 taps |
| 7 | >70% flow after 5-6 taps |
| 8 | 40-60% flow after 5-6 taps |
| 9 | 20-40% flow after 5-6 taps |
| 10 | 0-20% flow after 5-6 taps |

Sample Performance on DAP

| Sample ID | Time to coat in seconds | 48 hour pack test |
| --- | --- | --- |
| Sample 1 | 20 | 4 |
| Sample 2 | 24 | 5 |
| Sample 3 | 20 | 3 |
| Sample 4 | 15 | 2 |
| Sample 5 | 27 | 3 |
| Sample 6 | 26 | 4 |
| Sample 7 | 18 | 3 |
| Sample 8 | 14 | 2 |
| Sample 9 | 27 | 3 |
| Sample 10 | 34 | 5 |
| Sample 11 | 32 | 4 |
| Sample 12 | 25 | 4 |
| Sample 13 | 24 | 4 |
| Sample 14 | 24 | 4 |
| Sample 15 | 27 | 3 |
| Sample 16 | 29 | 5 |
| Sample 17 | 30 | 6 |
| Sample 18 | 21 | 2 |
| Sample 19* | 51 | 10 |
| Sample 20* | 56 | 10 |
| Sample 21 | 32 | 4 |
| Sample 22 | 28 | 4 |
| Sample 23 | 28 | 4 |

*Difficult to determine coating time as the color was streaky and not continuous.

EXAMPLE 27

200 grams of a technical grade of magnesium sulfate was charged to a glass 1000 ml beaker. The beaker was then placed under an overhead agitator with an anchor agitator blade. The height of the beaker was adjusted such that the bottom of the anchor agitator blade was close to the bottom of the glass beaker. The RPM of the overhead stirrer was adjusted to 200 RPM's and the magnesium sulfate was agitated for 30 seconds. After 30 seconds, a 2.0 gram of a sample of Example 21 was charged within 10 seconds. A stopwatch was used for timing to complete coating. (Visually: when 95% of magnesium sulfate particles were colored blue).

This was repeated for each of samples tested.

After coating, the 200 grams of coated magnesium sulfate was poured in a one quart jar and 200 grams of weight were placed on top of each sample in the quart jar. After setting for 48 hours, the weight was removed and a lid was placed on each quart jar. Each jar was then inverted and rated for flowability. If the contents of a jar did not flow in 5 minutes, a wooden handle of a 4 inch spatula was used to tap the jar to encourage flow. Flow rating is as follows:

| Rating | Action after inversion |
| --- | --- |
| 1 | Instant flow |
| 2 | >70% flow in 1 minute |
| 3 | >70% flow in 1-3 minutes |
| 4 | >70% flow in 3-5 minutes |
| 5 | >70% flow after 1-2 taps |
| 6 | >70% flow after 3-4 taps |
| 7 | >70% flow after 5-6 taps |
| 8 | 40-60% flow after 5-6 taps |
| 9 | 20-40% flow after 5-6 taps |
| 10 | 0-20% flow after 5-6 taps |

Sample Performance on Magnesium Sulfate

| Sample ID | Time to coat in seconds | 48 hour pack test |
| --- | --- | --- |
| Sample 1 | 22 | 4 |
| Sample 2 | 23 | 5 |
| Sample 3 | 20 | 4 |
| Sample 4 | 18 | 2 |
| Sample 5 | 27 | 3 |
| Sample 6 | 29 | 3 |
| Sample 7 | 17 | 3 |
| Sample 8 | 14 | 2 |
| Sample 9 | 29 | 3 |
| Sample 10 | 31 | 6 |
| Sample 11 | 33 | 4 |
| Sample 12 | 26 | 4 |
| Sample 13 | 36 | 4 |
| Sample 14 | 25 | 5 |
| Sample 15 | 28 | 3 |
| Sample 16 | 29 | 5 |
| Sample 17 | 30 | 6 |
| Sample 18 | 18 | 2 |
| Sample 19* | 54 | 10 |
| Sample 20* | 58 | 10 |
| Sample 21 | 33 | 4 |
| Sample 22 | 28 | 3 |
| Sample 23 | 28 | 3 |

*Difficult to determine coating time as the color was streaky and not continuous.

EXAMPLE 28

120 grams of prilled urea, 20 grams of fertilizer grade potassium sulfate, 40 grams of fertilizer grade diammonium phosphate, 10 grams of fertilizer grade zinc sulfate and 10 grams of fertilizer grade iron sulfate were charged to a glass 1000 ml beaker. The beaker was then placed under an overhead agitator with an anchor agitator blade. The height of the beaker was adjusted such that the bottom of the anchor agitator blade was close to the bottom of the glass beaker. The RPM of the overhead stirrer was adjusted to 200 RPM's and the contents of the compounded fertilizer were agitated for 30 seconds. After 30 seconds, a 2.0 gram of each sample to be tested was charged within 10 seconds. A stopwatch was used for timing to complete coating. (Visually: when 95% of magnesium sulfate particles were colored blue). This was repeated for each of the samples to be tested.

After coating, the 200 grams of coated compounded fertilizer was poured in a one quart jar and 200 grams of weight were placed on top of each sample in the quart jar. After setting for 48 hours, the weight was removed and a lid was placed on each quart jar. Each jar was then inverted and rated for flowability. If the contents of a jar did not flow in 5 minutes, a wooden handle of a 4 inch spatula was used to tap the jar to encourage flow. Flow rating is as follows:

| Sample ID | Time to cost in seconds | 48 hour pack test |
|---|---|---|
| Sample 1 | 18 | 3 |
| Sample 2 | 22 | 5 |
| Sample 3 | 23 | 3 |
| Sample 4 | 14 | 2 |
| Sample 5 | 26 | 3 |
| Sample 6 | 28 | 5 |
| Sample 7 | 20 | 3 |
| Sample 8 | 18 | 2 |
| Sample 9 | 25 | 3 |
| Sample 10 | 32 | 5 |
| Sample 11 | 28 | 4 |
| Sample 12 | 25 | 4 |
| Sample 13 | 26 | 3 |
| Sample 14 | 27 | 4 |
| Sample 15 | 27 | 3 |
| Sample 16 | 28 | 5 |
| Sample 17 | 28 | 6 |
| Sample 18 | 15 | 2 |
| Sample 19* | 47 | 8 |
| Sample 20* | 48 | 9 |
| Sample 21 | 29 | 5 |
| Sample 22 | 28 | 4 |
| Sample 23 | 29 | 5 |

*Difficult to determine coating time as the color was streaky and not continuous

| Rating | Action after inversion |
|---|---|
| 1 | Instant flow |
| 2 | >70% flow in 1 minute |
| 3 | >70% flow in 1-3 minutes |
| 4 | >70% flow in 3-5 minutes |
| 5 | >70% flow after 1-2 taps |
| 6 | >70% flow after 3-4 taps |
| 7 | >70% flow after 5-6 taps |
| 8 | 40-60% flow after 5-6 taps |
| 9 | 20-40% flow after 5-6 taps |
| 10 | 0-20% flow after 5-6 taps |

EXAMPLE 29

100 grams of uncoated "tall" fescue grass seeds was charged to a glass 1000 ml beaker. The beaker was then placed under an overhead agitator with an anchor agitator blade. The height of the beaker was adjusted such that the bottom of the anchor agitator blade was close to the bottom of the glass beaker. The RPM of the overhead stirrer was adjusted to 100 RPM's and the seeds were agitated for 30 seconds. After 30 seconds, a 2.0 gram of a sample was charged within 10 seconds. The seeds were agitated until 95% of the seeds were coated.

After coating, the 1 gram of coated seeds was added to 150 ml glass beaker in a manner to insure the seeds were equally distributed on the bottom of the beaker. The top of the beaker was sealed with a plastic wrap and placed in an dark environment at 30 C. The beaker was checked at 7, 14 and 21 days for signs of germination and rated for % of seeds that germinated.

After 60 days, the plastic wrap covering was slit and a prepared Contec test strip was inserted and placed just above the seed to test for presence of mold and mildew.

| Rating | % germination of seeds |
|---|---|
| 0 | None |
| 1 | 0-5% |
| 2 | 5-10% |
| 3 | 10-20% |
| 4 | 20-30% |
| 5 | >30% |

Sample Performance of Tall Fescue Grass Seed

| Sample ID | 7 days | 14 days | 21 days | Mold/mildew after 60 days |
|---|---|---|---|---|
| Sample 1 | 0 | 0 | 0 | No |
| Sample 2 | 0 | 0 | 0 | No |
| Sample 3 | 0 | 0 | 0 | No |
| Sample 4 | 0 | 0 | 0 | No |
| Sample 7 | 0 | 0 | 0 | No |
| Sample 8 | 0 | 0 | 0 | No |
| Sample 9 | 0 | 0 | 0 | No |
| Sample 10 | 0 | 0 | 0 | No |
| Sample 14 | 0 | 0 | 0 | No |
| Sample 18 | 0 | 0 | 0 | No |
| Sample 19 | 0 | 1 | 2 | Yes |
| Sample 20 | 0 | 1 | 2 | Yes |

The below table 1 summarizes the compositions that occur in each of the examples. The presence of an "X" in table 1 means that the particular example composition contains that particular component.

TABLE 1

| Example No. | DMSO | Glycerin | TPGME | Sorbitol | DMG | PG | DPG | EG | PC | TT | DD | AT | DMA |
|---|---|---|---|---|---|---|---|---|---|---|---|---|---|
| 1 | | | | | | | | | | X | | | |
| 2 | | | | | | | X | | | X | | | |
| 3 | | X | | | | | | | | X | | | |
| 4 | | | | X | | | | | | X | | | |
| 5 | | | | | | | | | | X | | | |
| 6 | | | | | | | | | | X | | | |

TABLE 1-continued

| Example No. | DMSO | Glycerin | TPGME | Sorbitol | DMG | PG | DPG | EG | PC | TT | DD | AT | DMA |
|---|---|---|---|---|---|---|---|---|---|---|---|---|---|
| 7 | | | | | | X | | X | | | | | |
| 8 | | X | | | | | | X | | | | | |
| 9 | | | | | | | | X | | | | | |
| 10 | X | | | | | | | | | | | | |
| 11 | X | | | | | | | | | | | | |
| 12 | | | | | | | | X | | | | | |
| 13 | | | | | | | | X | | | | | |
| 14 | X | | | | | | X | X | | | | | |
| 15 | X | | | | | | | | | | | | |
| 16 | | | | | | | | X | | | | | |
| 17 | | | | | | | | X | | | | | |
| 18 | | | | | | | | X | | | | | |
| 19 | X | | | X | | | | | | | | | |
| 20 | | | | | | X | | | | | | | |
| 21 | | X | | | | | | | | | | | |
| 22 | | X | | | | | | | | | | | |
| 23 | | X | | | | | X | | | | | | |
| 24 | | | | | | | | | X | | | | |
| 25 | | | | | | | | | X | | | | |

DMSO—dimethylsulfoxide
PG—propylene glycol
DPG—dipropylene glycol
DMG—Dimethyl Gluterate
TPGME—tripropylene glycol methyl ether
EG—ethylene glycol Samples from Examples 1-25 were evaluated for safety and environmental properties and the results are shown in the below Table 2:

TABLE 2

| Sample # | Human Health Rating | Flash Point ° F. | Aquatic Toxicity Rating |
|---|---|---|---|
| Ex 1 | 1.0 | >145° | Low |
| Ex 2 | 1.0 | >145° | Low |
| Ex 3 | 1.0 | >145° | Low |
| Ex 4 | 1.0 | >145° | Low |
| Ex 5 | 1.0 | >145° | Low |
| Ex 6 | 1.0 | >145° | Low |
| Ex 7 | 1.0 | >145° | Low |
| Ex 8 | 1.0 | >145° | Low |
| Ex 9 | 1.0 | >145° | Low |
| Ex 10 | 1.0 | >145° | Low |
| Ex 11 | 1.0 | >145° | Low |
| Ex 12 | 1.0 | >145° | Low |
| Ex 13 | 1.0 | >145° | Low |
| Ex 14 | 1.0 | >145° | Low |
| Ex 15 | 1.0 | >145° | Low |
| Ex 16 | 1.0 | >145° | Low |
| Ex 17 | 1.0 | >145° | Low |
| Ex 18 | 1.0 | >145° | Low |
| Ex 19 | 1.0 | <145° | Low |
| Ex 20 | 1.0 | >145° | Low |
| Ex 21 | 1.0 | >145° | Low |
| Ex 22 | 1.0 | >145° | Low |
| Ex 23 | 1.0 | >145° | Low |
| Ex 24 | 1.0 | >145° | Low |
| Ex 25 | 1.0 | >145° | Low |

The Human Health rating is based on HMIS (Hazardous Materials Information System) rating on Health of any organo solvent component >2%

The Flash Point is based on flash point of any organo solvent component >5%

The Aquatic Toxicity Rating is based on any organo solvent component at any level The following references are incorporated by reference in their entireties.

| | |
|---|---|
| 4,839,461 | Boehmke |
| 4,172,072 | Ashmead |
| 4,799,953 | Danzig |
| 4,813,997 | Kinnersley |
| 4,863,506 | Young |
| 5,059,241 | Young |
| 5,047,078 | Gill |
| 5,350,735 | Kinnersley |
| 5,593,947 | Kinnersley |
| 5,783,523 | Koskan |
| 5,814,582 | Koskan |
| 6,753,395 | Sanders |
| 6,756,461 | Sanders |
| 6,818,039 | Sanders |
| 8,043,995 | Sanders |
| 8,016,907 | Sanders |
| 8,025,709 | Sanders |
| 5,994,265 | Barclay |
| 7,001,869 | Johnson |
| 6,557,298 | Obert |

It is contemplated and therefore within the scope of the present invention that any feature that is described above can be combined with any other feature that is described above. When mixtures, formulations and/or compositions are discussed, it should be understood that those mixtures, formulations and/or compositions are contemplated as being parts of bigger mixtures, formulations and/or compositions. Further, if a composition is enumerated, methods using and methods of making that composition are contemplated and within the scope of the present invention. When a range is discussed, it is contemplated and therefore within the scope of the invention that any number that falls within that range is contemplated as an end point generating a plurality of sub-ranges within that range. For example if a range of 1-10 is given, 2, 3, 4, 5, 6, 7, 8, and 9 are contemplated as end points to generate a sub-range that fit within the scope of the enumerated range. Moreover, it should be understood that the present invention contemplates minor modifications that can be made to the compositions and methods of the present invention. In any event, the present invention is defined by the below claims.

We claim:
1. A composition comprising one or more Poly (organic acids), [P(OA)]s, and/or their salt(s) dissolved in one or more of a Non-aqueous Organo Solvent Delivery System (NOSDS), wherein said composition is a stable dispersion for coating man-made and/or natural fertilizer components and/or seeds wherein the [P(OA)]s are homopolymers, copolymers and/or terpolymers and wherein said homopolymers, copolymers and/or terpolymers are comprised of one or more of the following monomers:
aspartic acid, glutamic acid, maleic acid, itaconic acid, citraconic acid, citric acid, acrylic acid, methacrylic acid, itaconic acid, and citraconic acid, their $C_{1-6}$ esters, anhydrides, and imides, or their salts;
and wherein the NOSDS is comprised of:
a) one or more protic solvents selected from the group consisting of:
1) a C1-10 alcohol, 2) one or more polyols selected from the group consisting of trimethylol propane, trimethylol ethane, pentaerythritol, sorbitol, sorbitan, glucose, fructose, galactose, and glycerin, 3) poly(C1-10 alkylene) glycols, 4) one or more alkylene glycols selected from the group consisting of ethylene glycol, 1,3 propylene glycol, 1,2 propylene glycol, and butylene glycol, 5) isopropylidene glycerol 6) one or more alkylene glycol alkyl ethers selected from the group consisting of tripropylene glycol methyl ether, tripropylene glycol butyl ether, dipropylene glycol butyl ether and dipropylene glycol butyl ether, 7) ethyl, propyl, or butyl lactate, 8) one or more alkanolamines selected from the group consisting of ethanolamine, diethanolamine, dipropanolamine, methyl diethanolamine, monoisopropanolamine and triethanolamine and 9) glycerol carbonate and
b) one or more aprotic solvents selected from the group consisting of 1) dimethyl sulfoxide 2) a dialkyl sulfoxide, diaryl sulfoxide, or an alkylaryl sulfoxide having the formula:

$$R_1S(O)_xR_2$$

wherein $R_1$ and $R_2$ are each independently a $C_{1-6}$ alkyl group, an aryl group, or $C_{1-3}$ alkylenearyl group, or $R_1$ and $R_2$ with the sulfur to which they are attached form a 4 to 7 membered ring wherein $R_1$ and $R_2$ together are a $C_{1-6}$ alkylene group which optionally contains one or more atoms selected from the group consisting of O, S, Se, Te, N, and P in the ring and x is 1 or 2 or
3) an alkylene carbonate selected from the group consisting of ethylene carbonate, propylene carbonate and butylene carbonate, 4) a polyol capped with acetate or formate wherein the polyol portion is one or more of ethylene glycol, 1,3 propylene glycol, 1,2propylene glycol, butylene glycol, trimethylol propane, trimethylol ethane, pentaerythritol, sorbitol, sorbitan, glucose, fructose, galactose or glycerin, 5) an alkylene glycol alkyl ether acetates selected from the group consisting of dipropylene glycol methyl ether acetate, tripropylene glycol methyl ether acetate, and tripropylene glycol butyl ether acetate, 6) isophorone, 7) one or more members selected from the group consisting of dimethylsuccinate, dimethyl adipate, diethyl glutarate, and dimethyl glutarate, 8) one or more members selected from the group consisting of dimethylacetamide, dimethylformamide, and dimethyl-2-imidazolidinone 9) hexamethylphosphoramide, 10) one or more members selected from the group consisting of 1,2-dimethyloxyethane and 2-methoxyethyl ether, 11) cyclohexylpyrrolidone and 12) limonene and wherein the composition is substantially free of water.

2. The composition of claim 1, wherein the salts are derived from metals, metal hydroxides, metal alkylates, metal carbonates, ammonia, ammonium hydroxide, or organoamines.

3. The composition of claim 2, wherein the metals in the metals, metal hydroxides, metal alkylates, or metal carbonates comprise one or more of Na, K, Mg, Ca, Fe, Zn, Mn, Cu, Co, Mo or Ni.

4. The composition of claim 2, wherein the organoamines comprise one or more of mono $C_{1-6}$ amine, di $C_{1-6}$ amine, tri $C_{1-6}$ amine, mono ethanol amine, diethanol amine, triethanol amine, monoisopropanol amine, diisopropanol amine, triisopropanol amine, ethylene diamine diethylene triamine, triethylene tetraamine, or tetraethylene pentamine.

5. The composition of claim 1, wherein the composition comprises one or more protic solvents or one or more aprotic solvents.

6. The composition of claim 1, wherein the composition:
i has flashpoints above 145° F.;
ii has a human health rating of 1.0;
iii provides stable dispersions of [P(OA)]s or their salts at levels of 1 -50% in the NOSDS at storage temperatures down to at least 10° C.;
iv provides improved, even application of a coating to fertilizer granules and seeds while not causing clumping of the fertilizer granules, premature seed germination and does not support the growth of mold and mildew on seeds; and
v will not detrimentally impact the stability of alkyl thiophosphoric triamides.

7. The composition of claim 1, wherein the NOSDS comprises one or more protic solvents wherein the [P(OA)]s to the one or more protic solvent ratio is between about 90/10 to 10/90.

8. The composition of claim 1, wherein the one or more [P(OA)]s comprises a potassium salt of a polyaspartate wherein the potassium salt of the polyaspartate is present in an amount that is between about 10-45% of a total composition amount and the NOSDS of the formulation is ethylene glycol.

9. The composition of claim 1, further comprising one or more of surfactants, buffers, fragrance/odor masking agents, colorants, micro-nutrients, dispersed urease inhibitor(s), dispersed nitrification inhibitor(s), pesticide(s), fungicides(s), herbicide(s), insecticide(s) or flow modifiers.

10. A process for producing the composition of claim 1, wherein said process comprises procuring one or more of the following monomers:
aspartic acid, glutamic acid, maleic acid, itaconic acid, citraconic acid, citric acid, acrylic acid, methacrylic acid, itaconic acid, and citraconic acid, their anhydrides, and imides, or their salts;
wherein said one or more monomers is/are dispersed into one or more protic solvents at a molar ratio range of about 0.5/1 to 10/1 of NOSDS/ monomer and/or at a weight ratio of 10/90% to 90/10% of monomer/protic solvent which is heated to 120-190° C. to form an ester wherein the one or more protic solvents are selected from the group consisting of:
1) an alcohol from the family of $C_{1-10}$ alkanols, 2) polyols selected from the group consisting of trimethylol propane, trimethylol ethane, pentaerythritol, sorbitol, sorbitan, glucose, fructose, galactose, and glycerin, 3) poly($C_{1-10}$ alkylene) glycols, 4) alkylene glycols selected from the group consisting of ethylene glycol, 1,3 propylene glycol, 1,2 propylene glycol, and butylene glycol, 5) isopropylidene glycerol 6) alkylene glycol alkyl ethers selected from the group consisting of tripropylene glycol methyl ether, tripropylene glycol butyl ether, dipropylene glycol butyl ether and dipropylene glycol butyl ether, 7) ethyl, propyl, or butyl lactate, 8) an alkanolamine selected from the group consisting of ethanolamine, diethanolamine, dipropanolamine, methyl diethanolamine, monoisopropanolamine and triethanolamine and 9) glycerol carbonate;

and heating said dispersion to a polymerization temperature with or without catalyst, until a molecular weight of 1500 to 10000 g/mol is achieved wherein water is removed with a vacuum of 200 mm or less thereby resulting in a composition comprising one or more Poly (organic acids), [P(OA)]s, and/or their salt(s) dissolved in one or more protic NOSDS, wherein said composition is a stable dispersion for coating man-made and natural fertilizer components and/or seeds and wherein the composition is substantially free of water, and to which one or more aprotic solvents is added wherein said aprotic solvents comprise one or more members selected from the group consisting of 1) dimethyl sulfoxide 2) dialkyl, diaryl, or alkylaryl sulfoxide(s) having the formula:

$$R_1S(O)_xR_2$$

wherein $R_1$ and $R_2$ are each independently a $C_{1-6}$ alkylene group, an aryl group, or $C_{1-3}$alkylenearyl group or $R_1$ and $R_2$ with the sulfur to which they are attached form a 4 to 7membered ring wherein $R_1$ and $R_2$ together are a $C_{1-6}$ alkylene group which optionally contains one or more atoms selected from the group consisting of O, S, Se, Te, N, and P in the ring and x is 1 or 2;

3) alkylene carbonates selected from the group consisting of ethylene carbonate, propylene carbonate and butylene carbonate, 4) polyols capped with acetate or formate wherein the polyol is one or more of ethylene glycol, 1,3 propylene glycol, 1,2 propylene glycol, butylene glycol, trimethylol propane, trimethylol ethane, pentaerythritol, sorbitol, sorbitan, glucose, fructose, galactose and/or glycerin, 5) alkylene glycol alkyl ethers acetates selected from the group consisting of dipropylene glycol methyl ether acetate, tripropylene glycol methyl ether acetate, and tripropylene glycol butyl ether acetate, 6) isophorone, 7) dimethylsuccinate, dimethyl adipate, diethyl glutarate, dimethyl glutarate, 8) dimethylacetamide, dimethylformamide, dimethyl-2-imidazolidinone 9) hexamethylphosphoramide, 10) 1,2-dimethyloxethane, 2-methoxyethyl ether, 11) cyclohexylpyrrolidone and 12) limonene wherein said composition is a stable dispersion for coating man-made and natural fertilizer components and/or seeds and wherein the composition is substantially free of water.

11. The process of claim 10, wherein said ester is further saponified generating a carboxylic acid salt wherein said salt is derived from metals, metal hydroxides, metal alkylates, metal carbonates, ammonia, ammonium hydroxide, or organoamines wherein water resulting from neutralization or from addition of aqueous solutions of alkalis is removed by stripping by elevated temperature or through a combination of temperature and vacuum , molecular sieves , drying agents and/or filtration.

12. The process of claim 11, wherein a metal in the metals, metal hydroxides, metal alkylates, or metal carbonates is Na, K, Mg, Ca, Fe, Zn, Mn, Cu, Co, Mo and/or Ni.

13. The process of claim 11, wherein the organoamines comprise one or more of mono $C_{1-6}$ amine, di $C_{1-6}$ amine, tri $C_{1-6}$ amine, mono ethanol amine, diethanol amine, triethanol amine, monoisopropanol amine, diisopropanol amine, triisopropanol amine, ethylene diamine diethylene triamine, triethylene tetraamine, or tetraethylene pentamine.

14. A process for producing a composition wherein said process comprises procuring one or more of the following monomers:

aspartic acid, glutamic acid, maleic acid, itaconic acid, citraconic acid, citric acid, acrylic acid, methacrylic acid, itaconic acid, and citraconic acid, their $C_{1-6}$esters, anhydrides, and imides, or their salts; and dispersing said one or more monomers into an aprotic solvent to create a dispersion wherein said aprotic solvent is one or more members selected from the group consisting of 1) dimethyl sulfoxide 2) dialkyl, diaryl, or alkylaryl sulfoxide(s) having the formula:

$$R_1S(O)_xR_2$$

wherein $R_1$ and $R_2$ are each independently a $C_{1-6}$ alkylene group, an aryl group, or $C_{1-3}$alkylenearyl group or $R_1$ and $R_2$ with the sulfur to which they are attached form a 4 to 8membered ring wherein $R_1$ and $R_2$ together are a $C_{1-6}$ alkylene group which optionally contains one or more atoms selected from the group consisting of O, S, Se, Te, N, and P in the ring and x is 1 or 2;

3) an alkylene carbonate selected from the group consisting of ethylene carbonate, propylene carbonate and butylene carbonate, 4) a polyol capped with acetate or formate wherein the polyol is one or more of ethylene glycol, 1,3 propylene glycol, 1,2 propylene glycol, butylene glycol, trimethylol propane, trimethylol ethane, pentaerythritol, sorbitol, sorbitan, glucose, fructose, galactose and glycerin, 5) an alkylene glycol alkyl ether acetate selected from the group consisting of dipropylene glycol methyl ether acetate, tripropylene glycol methyl ether acetate, and tripropylene glycol butyl ether acetate, 6) isophorone, 7) dimethylsuccinate, dimethyl adipate, diethyl glutarate, dimethyl glutarate, 8) dimethylacetamide, dimethylformamide, dimethyl-2-imidazolidinone 9) hexamethylphosphoramide, 10) 1,2-dimethyloxethane, 2-methoxyethyl ether, 11) cyclohexylpyrrolidone and 12) limonene; heating said dispersion to a polymerization temperature with or without a catalyst, held at polymerization temperature until a molecular weight of 1500 to 10000 grams/mol is achieved, wherein water is removed by a vacuum of 200 mm or less, thereby resulting in a composition comprising one or more Poly (organic acids), [P(OA)]s, and/or their salt(s) dissolved in one or more aprotic NOSDS, wherein said composition is a stable dispersion for coating man-made and natural fertilizer components and/or seeds, and further resulting in a composition that is substantially free of water.

15. The process of claim 14, further comprising neutralizing the one or more monomers with one or more metals, wherein said one or more metals comprise elemental metals, metal oxides, metal hydroxides, metal alkylates or metal carbonates, or with one or more nitrogen containing compounds comprising ammonia, ammonium hydroxide, or organoamines wherein water resulting from neutralization or from addition of aqueous solutions of alkalis is removed by stripping the composition by using an elevated temperature or by a combination of temperature with vacuum, by molecular sieves, or by drying agents and filtration.

16. The process of claim 15, wherein the one or more metals in the elemental metals, metal oxides, metal hydroxides, metal alkylates or metal carbonates comprise Na, K, Mg, Ca, Fe, Zn, Mn, Cu, Co, Mo or Ni.

17. The process of claim 15, wherein the organoamines comprise one or more of mono $C_{1-6}$ amine, di $C_{1-6}$ amine, tri $C_{1-6}$ amine, mono ethanol amine, diethanol amine, triethanol amine, monoisopropanol amine, diisopropanol amine, tri-isopropanol amine, ethylene diamine diethylene triamine, triethylene tetraamine, or tetraethylene pentamine.

18. A process for producing a composition wherein said process comprises procuring a polymer that comprises polysuccinimide, polyaspartic acid, polyglutamic acid, and/or a copolymer of aspartic acid and glutamic acid and/or salts thereof;
wherein
said polymer is dispersed within a NOSDS at a % weight ratio of 10:90% to 90:10% of polymer:NOSDS, wherein the NOSDS comprises a) one or more protic solvents which are heated to 120-190° C. to form an ester and wherein the one or more protic solvents are selected from the group consisting of::
1) an alcohol from the family of $C_{1-10}$ alkanols, 2) polyols selected from the group consisting of trimethylol propane, trimethylol ethane, pentaerythritol, sorbitol, sorbitan, glucose, fructose, galactose, and glycerin, 3) poly($C_{1-10}$ alkylene) glycols, 4) alkylene glycols selected from the group consisting of ethylene glycol, 1,3 propylene glycol, 1,2 propylene glycol, and butylene glycol, 5) isopropylidene glycerol 6) alkylene glycol alkyl ethers selected from the group consisting of tripropylene glycol methyl ether, tripropylene glycol butyl ether, dipropylene glycol butyl ether and dipropylene glycol butyl ether, 7) ethyl, propyl, or butyl lactate, 8) an alkanolamine selected from the group consisting of ethanolamine, diethanolamine, dipropanolamine, methyl diethanolamine, monoisopropanolamine and triethanolamine and 9) glycerol carbonate wherein water is removed through a vacuum of 200 mm or less thereby resulting in a composition comprising one or more Poly (organic acids), [P(OA)]s, and/or their salt(s) dissolved in one or more protic NOSDS, wherein said composition is a stable dispersion for coating man-made and natural fertilizer components and/or seeds and wherein the composition is substantially free of water.

19. The process of claim 18, wherein the ester is saponified generating a carboxylic acid salt wherein said salt is derived from metals, metal hydroxides, metal alkylates, metal carbonates, ammonia, ammonium hydroxide, or organoamines wherein water resulting from neutralization or from addition of aqueous solutions of alkalis is removed by stripping at elevated temperature or a combination of temperature and vacuum, molecular sieves, drying agents and filtration.

20. The process of claim 19, wherein the salts are derived from metals, metal hydroxides, metal alkylates, metal carbonates, ammonia, ammonium hydroxide, or organoamines and the metal in the metals, metal hydroxides, metal alkylates, or metal carbonates are one or more of Na, K, Mg, Ca, Fe, Zn, Mn, Cu, Co, Mo or Ni.

21. The process of claim 20, wherein the organoamines comprise one or more of mono $C_{1-6}$ amine, di $C_{1-6}$ amine, tri $C_{1-6}$ amine, mono ethanol amine, diethanol amine, triethanol amine, monoisopropanol amine, diisopropanol amine, tri-isopropanol amine, ethylene diamine diethylene triamine, triethylene tetraamine, or tetraethylene pentamine.

* * * * *